United States Patent [19]

Schirlin et al.

[11] Patent Number: 5,559,140
[45] Date of Patent: Sep. 24, 1996

[54] DIFLUORO STATONE ANALOGS

[75] Inventors: Daniel Schirlin, Lampertheim; Viviane Van Dorsselaer; Céline Tarnus, both of Strasbourg, all of France

[73] Assignee: Merrell Pharmaceuticals Inc., Cincinnati, Ohio

[21] Appl. No.: 81,368

[22] PCT Filed: Dec. 20, 1991

[86] PCT No.: PCT/US91/09741

§ 371 Date: Jun. 30, 1993

§ 102(e) Date: Oct. 29, 1993

[87] PCT Pub. No.: WO92/12123

PCT Pub. Date: Jul. 23, 1993

[30] Foreign Application Priority Data

Jan. 2, 1991 [EP] European Pat. Off. ............ 91400005

[51] Int. Cl.$^6$ .................................................. A61K 31/44
[52] U.S. Cl. ................. 514/357; 514/620; 514/237.5; 514/307; 546/335; 546/170; 546/337; 546/145; 549/441; 556/419; 560/27; 564/157; 564/158; 564/165; 544/168; 544/162

[58] Field of Search .................... 564/158, 157, 564/165; 546/335, 170, 337, 145; 549/441; 556/419; 560/27; 544/168, 162; 514/357, 314, 486, 466, 619, 620, 237.5, 307

[56] References Cited

FOREIGN PATENT DOCUMENTS

| 0352000 | 1/1990 | European Pat. Off. . |
|---|---|---|
| 2171103 | 8/1986 | United Kingdom . |
| 2203740 | 10/1988 | United Kingdom . |
| 2212158 | 7/1989 | United Kingdom . |
| 8606379 | 11/1986 | WIPO . |

OTHER PUBLICATIONS

T. W. Graham Solomons, Organic Chemistry, Second Edition, 1980, pp. 657–660.

*Primary Examiner*—Samuel Barts
*Attorney, Agent, or Firm*—Carolyn D. Moon

[57] ABSTRACT

This invention relates to novel difluoro statone analogs, to the processes and intermediates useful for their preparation and to their use as anti-viral agents.

11 Claims, No Drawings

DIFLUORO STATONE ANALOGS

This application was filed under U.S.C. 371 from the application PCT/US 91/096741 filed Dec. 20, 1991.

This invention relates to novel difluoro statone analogs, to the processes and intermediates useful for their preparation and to their use as anti-vital agents.

BACKGROUND INFORMATION

EP 352 000 A3 discloses retrovital protease binding peptides useful in inhibiting protease activity add in treating vital disease which differ structurally from the compounds of the present invention.

DESCRIPTION OF THE PRESENT INVENTION

More specifically this invention relates to novel difluoro statone analogs of the formula $$R_1 \left[ \begin{array}{c} P_2 \\ | \\ CNHCH \\ || \\ O \end{array} \right]_x \begin{array}{c} P_1 \\ | \\ CNHCHC-CF_2C-NR_5R_6 \\ || \quad || \quad || \\ O \quad\, O \quad\, O \end{array} \quad I$$

and the hydrates, isosteres and the pharmaceutically acceptable salts thereof wherein x in zero or one, $P_1$ is Q, or B, B being $$CH_2-\!\!\!\!\!\bigcirc\!\!\!\!\!-\![(CH_2)_a-(O)_b-(CH_2)_c-R]_d$$

with the proviso that B is other than p-hydroxybenzyl or p-alkoxybenzyl, a is zero, 1, 2 or 3, b is zero or 1, c is zero, 1, 2, 3, 4 or 5, d is 1 or 2, e is zero, 1 or 2, Q is $$(CH_2)_d-\!\!\!\!\!\bigcirc\!\!\!\!\!\!\begin{array}{c}O\\ \\O\end{array}\!\!\!\!\!(CH_2)_d,$$

$P_2$ is $C_{1-6}$ alkyl, cyclopentyl, cyclohexyl, hydroxy $C_{1-6}$ alkylene, or

[structure: difluorocyclopentane-N—T]

with T being H or $C(O)R_4$,

R is —$CH_2CHO$, hydroxy $C_{1-6}$ alkylene, $C_{1-6}$ alkoxy $C_{1-6}$ alkylene, $C_{1-6}$ alkyl, phenyl $$-\!\!\!\!\!\bigcirc\!\!\!\!\!-(R_3)_d$$

or Q, $R_1$ is benzyloxy, $C_{1-6}$ alkoxy, $C_{1-6}$ alkyl, phenyl, benzyl, phenethyl, fluorenylmethylenoxy, 2-isoquinolinyl, PDL, $$CH_2N-(CH_2)_3CH_2, \; O-(CH_2)_2-N-CH_2CH_2,$$

$NHSO_2R_4$, $N(R_4)$(benzyl), and $N(R_4)$(PDL), with PDL being —$(CH_2)_a$-2-, 3-, or 4-pyridyl, or p-W-substituted benzyloxy with W being nitro, OH amino, $C_{1-6}$ alkoxy, hydroxy $C_{1-6}$ alkylene, or halogeno, $R_3$ is $C_{1-6}$ allenyl, $C_{1-6}$ alkoxy, $C_{1-6}$ alkoxy, $C_{1-6}$ alkylene, hydroxy $C_{1-6}$ alkylene, $C_{1-6}$ alkyl H or OH, $R_4$ is H, $C_{1-6}$ alkyl, phenyl or benzyl, $R_5$ is H, $C_{1-6}$ alkyl, OH, $C_{1-6}$ alkoxy, $$-(CH_2)_d-\!\!\!\!\!\bigcirc\!\!\!\!\!-(V)_e,$$

V being $OR_4$ or hydroxy $C_{1-6}$ alkylene, $CH_2Si(CH_3)_2(R_3)$, —$(CH_2)_d$-Q, PDL, —N—$(CH_2)_2$—O—$CH_2CH_2$,   HO—[indanyl]—$(CH_2)_b$, $$CH_2-\!\!\!\!\!\!<\!\!\!\!\!\begin{array}{c}N\\ \\N\end{array}\!\!\!\!\!-\!\!\!\!\!\bigcirc,$$

—($C_{1-6}$ alkylene-)$OR_4$ or —CH(Y)(Z), Y being hydroxy $C_{1-6}$ alkylene, $C_{1-6}$ alkyl, or $(CH_2)_e C_6H_4$-(V)$_e$, and Z being CHO, $CO_2R_4$, $CO_2NHR_4$ or $(CH_2)_e OR_4$, $R_6$ is as defined for $R_5$ with the proviso that $R_6$ is other than H when $R_5$ is H, and when $R_5$ and $R_6$ are taken together with nitrogen atom to which they are attached form a heterocyclic moiety of the formulae

—N(CH$_2$)$_3$CH$_2$,  —N(CH$_2$)$_4$CH$_2$,  —N(CH$_2$)$_2$OCH$_2$CH$_2$, (a)                (b)                     (c)

(d) [benzo-fused N-heterocycle with $(CH_2)_b$]    (e) [R$_3$—Si—CH$_2$-N-R$_7$]

(f) [decahydroisoquinoline with R$_7$]    or  —N(CH$_2$)$_2$N—CH$_2$CH$_2$, | CH(O)

(g)

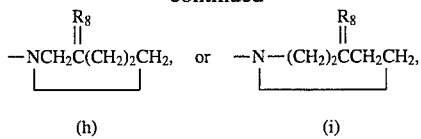

(h)   (i)

$R_7$ is $CH_2OR_4$ or $C(O)NHR_4$, $R_8$ is (H,OH) or =O.

Isosteres of the compounds of Formula I include those wherein (a) the α-amino acid residues of the $P_1$ and $P_2$ substituents are in their unnatural configuration (when there is a natural configuration) or (b) when the normal peptidic carbamoyl linkage is modified, such as for example, to form —$CH_2NH$— (reduced),

(N-methylamide), —$COCH_2$— (keto), —$CH(OH)CH_2$— (hydroxy), —$CH(NH_2)CH_2$— (amino), —$CH_2CH_2$— (hydrocarbon). Preferably a compound of the invention should not be in an isosteric form. Unless otherwise stated the a-amino acids are preferably in their L-configuration.

A compound of the invention may be in free form, e.g., amphoteric form, or in salt, e.g., acid addition or anionic salt, form. A compound in free form may be converted into a salt form in an art-known manner and vice-versa. Examples of salt forms are the trifluoroacetate, hydrochloride, sodium, potassium and ammonium forms, although the scope of salts embraced herein is not limited thereto, the scope includes all of the salts known to be useful in the art of peptide chemistry.

The pharmaceutically acceptable salts of the peptide of Formula I (in the form of water, or oil-soluble or dispersible products) include the conventional non-toxic salts or the quaternary ammonium salts of these peptides, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The hydrates of the compounds of Formula I are hydrated compounds having the partial structure

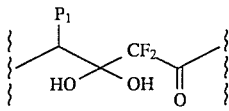

and in their end-use application are generally the active forms.

In general, as used herein, the term "alkyl" includes the straight, branched-chain and cyclized manifestations thereof, particularly such moieties as methyl, ethyl, isopropyl, n-butyl, t-butyl, —$CH_2$-t-butyl, cyclopropyl, n-propyl, pentyl, cyclopentyl, n-hexyl, cyclohexyl and cyclohexylmethyl. The term "aralkyl", when used, includes those aryl moieties attached to an alkylene bridging moiety, preferably methyl or ethyl. The term "aryl", when used, includes both carbocyclic and heterocyclic moieties. Preferred aryl and aralkyl moieties are phenyl, benzyl, naphthylmethyl, phenethyl and 2-pyridylmethyl. The fluorenylmethyloxy moiety is that moiety generally called by its abbreviation FMOC, and is the fluorenyl moiety bearing —$CH_2O$ attached to the 9-position of the fluoroenyl moiety.

More specifically, in the instance wherein $P_2$ is either $C_{1-6}$ alkyl or hydroxy $C_{1-6}$ alkylene, such moieties as $C(CH_3)_3$, —$CH(CH_3)_2$, —$CH(CH_3)(C_2H_5)$, —$C(OH)(CH_3)_2$ and —$CH(OH)CH_3$ are preferred. The "hydroxy $C_{1-6}$ alkylene" moiety is illustrated by —$CH_2$—OH, the "$C_{1-6}$ alkoxy $C_{1-6}$ alkylene" moiety, is illustrated by —$CH_2$—$OCH_3$, (although in each instance the $C_{1-6}$ alkylene may be straight or branched and the hydroxy radical is not limited to the terminal carbon atom of the alkylene moiety), the

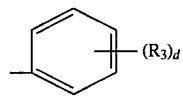

moiety is illustrated by benzyl, phenethyl, each of which may be substituted with one or two of the $R_3$ moieties (said moieties being the same or different). Similarly, in the instance when $P_1$ is $[(CH_2)_a—(O)_b—(CH_2)_cR]_d$, the R, a, b, c, moieties need not be identical when d is other than one, and, of course, when d is one a, b and c need not be identical.

As it is often quite advantageous to have what is termed an amino protecting group, the scope of those compounds of Formula I, includes those $R_1$ moieties which, together with their adjacent carbonyl moiety form such groups as acetyl (Ac), succinyl (Suc), benzoyl (Bz), t-butyloxycarbonyl (Boc), benzyloxycarbonyl (CBZ), tosyl (Ts), dansyl (DNS), isovaleryl (Ira), methoxysuccinyl (MeOSuc), 1-adamantanesulphonyl (AdSO$_2$), 1-adamantaneacetyl (AdAc), phenylacetyl, t-butylacetyl (Tba), bis[(1 -naphthyl)-methyl] acetyl (BNMA) and Rz wherein Rz is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolo, and acylsulfonamido (i.e., acylaminosulfonyl and sulfonylaminocarbonyl) containing from 1 to 15 carbons, provided that when the acylsulfonamido contains an aryl the aryl may be further substituted by a member selected from fluoro, chloro, bromo, iodo and nitro.

In those instances wherein there is an Rz moiety, it is preferred that Rz represent acylsulfonamido, particularly those wherein the acylsulfonamido contains an aryl moiety (preferably phenyl) substituted by a halogen. The preferred —A—Rz moieties being 4-[(4-chlorophenyl)sulfonylaminocarbonyl]phenylcarbonyl, 4-[(4-bromophenyl)sulfonylaminocarbonyl]-phenylcarbonyl and 4-[phenylsulfonylaminocarbonyl]-phenylcarbonyl (said moieties being abbreviated as 4-Cl-Ø-SAC-Bz, 4-Br-Ø-SAC-Bz and Ø-SAC-Bz, respectively).

In general the compounds of this invention may be prepared using standard chemical reactions analogously known in the art.

In the instance wherein it is desired to prepare compounds of the formula

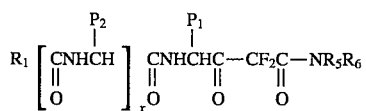

wherein $R_1$, $P_2$, $P_1$, $R_5$ and $R_6$ are as previously defined, the process outlined by the following reaction scheme may advantageously be utilized.

about 1–12 hours or ultrasonicated to produce compounds (4). Step (b) to obtain compounds (5) may be effected directly or undirectly. In one instance, the esters of Formula (4) are de-esterified using a strong base (LiOH, KOH, NaOH and the like) in the presence of water using a partially water miscible solvent (such as tetrahydrofuran, dimethoxyethane, dioxane) at about room temperature. The so-obtained de-esterified compound is then aminated with the appropriate $R_5R_6$-substituted amine using a peptide-like coupling procedure—i.e., using a mixed anhydride method using DCC and hydroxybenzotriazole at room temperature in solvents such as $CH_2Cl_2$, tetrahydrofuran or dimethylformamide. Alternatively the esters (4) may be directly subjected to a reaction with the appropriate $R_5R_6$-substituted amine without or with a solvent (tetrahydrofuran) at about 80° C. Following the preparation of compounds (5), the protecting groups Pg may readily be removed by standard procedures, e.g., hydrogenation or acid base hydrolysis. Compounds (6) are subjected to a peptide coupling procedure with an appropriately protected acid of the formulae $R_1CONH(P_2)COOH$ or $R_1CO_2H$, using the herein-described procedures (or by any other coupling procedure

REACTION SCHEME A

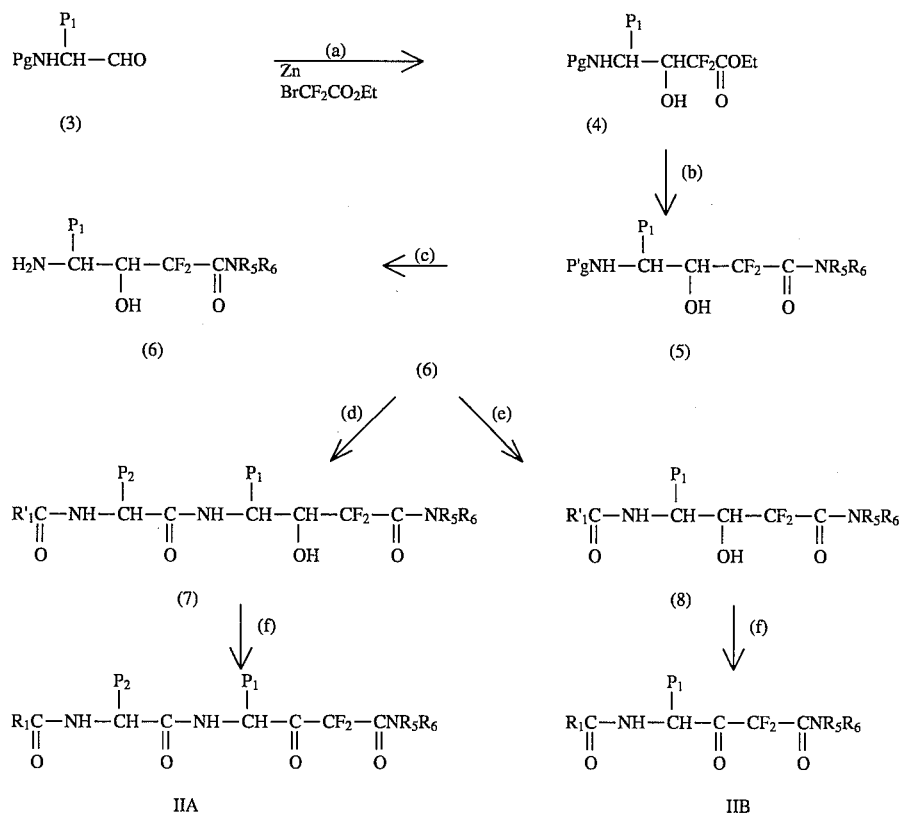

wherein $R'_1$ represents optional amino protecting groups, as herein above defined, and the $R_1$, $P_1$, $P_2$, $R_5$ and $R_6$ moieties are as previously defined.

In effecting the foregoing reaction scheme, the process is initiated by conducting a Reformatsky-type reaction wherein an aldehyde of Formula (3) is subjected to a condensation reaction with an ester of bromodifluoroacetic acid, preferably the ethyl ester in the presence of zinc and in an anhydrous aprotic solvent, e.g., tetrahydrofuran, ether, dimethoxyethane and the like under a nitrogen or argon inert atmosphere. The reaction is gently heated to about 60° C. for currently available) to produce compounds (7) and (8), respectively. At this point, if desired, the amide formed with $R_1$ may be optionally deprotected, or if desired, the amide may be replaced with another amide within the scope of $R_1$. The alcohols of (7) and (8) are then oxidized to the corresponding ketones and, if desired, the compounds may be converted to their pharmaceutically acceptable salts.

The oxidation may be effected via the well-known Swern oxidation procedure, or with 1,1,1-triacetoxy-2,1-benzoxiodol. The coupling procedures are effected according to standard procedures well known in the art.

In general the Swern oxidation [see Synthesis, (1981), 165] is effected by reacting about 2 to 10 equivalents of dimethylsulfoxide (DMSO) with about 1 to 5 equivalents of trifluoromethylacetic anhydride [$(CF_3CO)_2O$] or oxalyl chloride [$(COCl)_2$], said reactants being dissolved in an inert solvent, e.g., methylene chloride ($CH_2Cl_2$), said reaction being under an inert atmosphere (e.g., nitrogen or equivalently functioning gas) under anhydrous conditions at temperatures of about −70° C. to −30° C. to form an in situ sulfonium adduct to which is added about 1 equivalent of the appropriate alcohols, i.e., compounds (7) and (8). Preferably, the alcohols are dissolved in an inert solvent, e.g., $CH_2Cl_2$ or minimum amounts of DMSO, and the reaction mixture is allowed to warm to about −50° C. (for about 10–20 minutes) and then the reaction is completed by adding about 3 to 10 equivalents of a tertiary amine, e.g., triethylamine, N-methyl morpholine, etc.

Another alternative process for converting the alcohols to the desired ketones is an oxidation reaction which employs periodane (i.e., 1,1,1-triacetoxy-2,1-benzoxiodol), [see Dess Martin, *J. Org. Chem.*, 48, 4155, (1983)]. This oxidation is effected by contacting about 1 equivalent of the alcohols with 1 to 5 equivalents of periodane (preferably 1.5 equivalents), said reagent being in suspension in an inert solvent (e.g., methylene chloride) under an inert atmosphere (preferably nitrogen) under anhydrous conditions at 0° C. to 50° C. (preferably room temperature) and allowing the reactants to interact for about 1 to 48 hours. Optional deprotection of the amine protecting groups may be effected as desired after the ketones have been isolated.

Alternatively, 1 to 5 equivalents of a chromic anhydride-pyridine complex (i.e., a Sarett reagent prepared in situ) [see Fieser and Fieser "Reagents for Organic Synthesis" Vol. 1, pp. 145 and Sarett, et al., J.A.C.S. 25, 422, (1953)] said complex being prepared in situ in an inert solvent (e.g., $CH_2Cl_2$) in an inert atmosphere under anhydrous conditions at 0° C. to 50° C. to which complex is added 1 equivalent of the alcohols allowing the reactants to interact for about 1 to 15 hours, followed by isolation and optionally removing amine protecting groups.

For the preparation of the necessary aldehydes of (3), and the preparation of the acids which are to be coupled with the amines of Formula (6), alternative alkylation procedures are utilized depending upon whether the $P_1$ and/or the P moieties are or are not residues of natural amino acids. The preparation of these intermediates wherein the $P_1$ or $P_2$ moieties are residues of natural amino acids (or minor modifications thereof, e.g., $P_1$ or $P_2$ being a methyl ether of tyrosine), the compounds are either known or are prepared by processes and techniques well known in the art.

To prepare the intermediates of the formula $$\underset{(9)}{\overset{P_3}{\underset{|}{PgHN-CHCO_2R_9}}}$$

wherein Pg is an amino protecting group, $P_3$ is either a $P'_1$ or $P'_2$ moiety with $P'_1$ and being $P'_2$ as defined for $P_1$ and $P_2$ respectively, except that they are other than residues of naturally occuring amino acids, and the $R_9$ moiety is an alkyl radical, preferably methyl when $P_3$ is $P'_1$, and ethyl when $P_3$ is $P'_2$, alternative methods are available.

To prepare the intermediates of formulae

(10B)

(10A)

the following reaction scheme may be utilized

REACTION SCHEME B

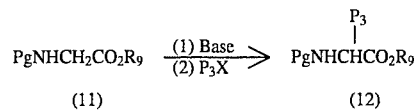

wherein $P_3$ is as previously defined and X is a leaving group, preferably halo or triflate, $R_9$ is methyl when $P_3$ is $P'_1$, and ethyl when $P_3$ is $P'_2$.

In essence, the preparation of compounds (12) utilizes the Krapcho method [Tetrahedron Letters, 26, 2205 (1976)] for alkylation wherein compounds (11) are treated with a base, e.g., LDA, (lithium diisopropylamide), followed by reaction with the desired $P_3X$ in the presence of TMEDA (i.e. tetramethylethylenediamine) in a solvent (tetrahydrofuran) with or without HMPA (i.e. hepamethyl-phosphonamide) according to the standard Krapcho conditions. Following alkylation the compounds are then subjected to a reduction using diisobutyl aluminum hydride (Dibal) in a mixture of solvents, e.g., ether, toluene, hexane, tetrahydrofuran at about −78° C. for about 1 hour. Following the preparation of the aldehydes of Formula (10B), the compounds are subjected to the processes of Reaction Scheme A.

Alternatively, the compounds of (12) may be prepared by a Malonate/Curtius type sequence of reactions, [see Yamada, et al., J. Amer. Chem. Soc., (1972) 94, 6203] as illustrated by the following reaction scheme

REACTION SCHEME C

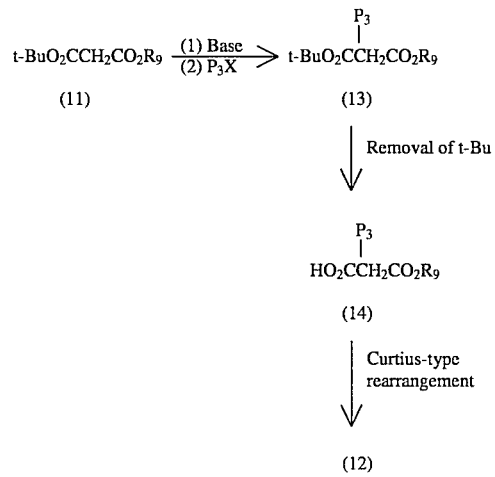

wherein t-Bu is t-butyl, although other selectively removal acid protecting groups may be utilized, and $P_3X$ is as previously defined. This reaction involves the alkylation of the malonate ester (11) followed by selective removal of the t-butyl protecting group to produce compounds (14). These compounds are then transformed to (12) using the Curtius type rearrangement which entails their conversion to the protected amine via the intermediately formed azides, isocyanates, amines which are then protected with standard amino protecting groups, preferentially being protected in situ.

In the instance wherein $P_3$ represents a $P'_1$ moiety, the ester is transformed to the desired aldehydes of Formula (3)

using standard Dibal reduction techniques, particularly in this situation (wherein $P_1$ is not a residue of a natural amino acid). Alternatively, (as is preferred when $P_1$ is a residue of a natural amino acid) the ester is de-esterified to its corresponding acid, converted to its corresponding hydroxamate and the hydroxamate upon treatment with lithium aluminum hydride is converted to its aldehyde. In the instance wherein $P_3$ represents a $P'_2$ moiety, the ethyl ester of compounds (12) are removed and the resulting compounds are ready for coupling as outlined in Reaction Scheme A.

Among the classes of amino protecting groups contemplated are: (1) acyl type protecting groups such as formyl, trifluoroacetyl, phthalyl, p-toluenesulfonyl (tosyl), benzenesulfonyl, nitrophenylsulfenyl, tritylsulfenyl, O-nitrophenoxyacetyl, and α-chlorobutyryl; (2) aromatic urethane type protecting groups such as benzyloxycarbonyl and substituted benzyloxycarbonyls such as p-chlorobenzyloxycarbonyl, p-methoxybenzyloxycarbonyl, p-nitrobenzyloxycarbonyl, p-bromobenzyloxycarbonyl, 1-(p-biphenylyl)-1-methylethoxycarbonyl, α-,α-dimethyl-3,5-dimethoxybenzyloxycarbonyl, and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl, and allyloxycarbonyl; (4) cycloalkyl urethane type protecting groups such as cyclopentyloxycarbonyl, adamantyloxycarbonyl, and cyclohexyloxycarbonyl; (5) thio urethane type protecting groups such as phenylthiocarbonyl; (6) alkyl type protecting groups such as triphenylmethyl (trityl) and benzyl (Bzl); (7) trialkylsilane protecting groups such as trimethylsilane if compatible. The preferred α-amino protecting groups are tert-butyloxycarbonyl (Boc) or benzyloxycarbonyl (CBZ). The use of Boc as an α-amino protecting group for amino acids is described by Bodansky et al. in "The Practice of Peptide Synthesis", Springer-Verlag, Berlin (1984), p. 20.

Having generically described the methods for the preparation of the compounds of this invention, the following specific examples illustrate the chemistry and techniques by which the synthesis may be effected.

EXAMPLE 1

4-(N-BENZYLOXYCARBONYL-L-VALYL) AMINO-2,2-DIFLUORO-3-OXO-5 -(4-BENZYLOXY)PHENYL-N-BENZYL PENTANAMIDE

Step A:

N-tert-Butoxycarbonyl-L-O-benzyltyrosine-N,O-dimethylhydroxamate

A mixture of N-tert-butoxycarbonyl-L-O-benzyltyrosine (37.1 g, 100 mmol), dicyclohexylcarbodiimide (20.6 g, 100 mmol) and N-hydroxybenzotriazole, hydrate (15.3 g, 100 mol) in anhydrous dichloromethane (350 ml) was stirred at 0° C. for 10 minutes. To that mixture were added, at 0° C., N,O-dimethylhydroxylamine hydrochloride (9.75 g, 100 mmol) and N-methylmorpholine (10.1 g, 100 mmol). The temperature was allowed to raise to room temperature while the stirring was continued for 15 hours. The white precipitate was filtered off, rinsed with dichloromethane. The filtrate was evaporated to dryness. The crude mixture was purified by flash chromatography (silica gel, ethyl acetate/cyclohexane: 2/8). 34.3 g of the expected hydroxamate were isolated as a white solid (83% yield). Rf: 0.36 (ethyl acetate/cyclohexane: 1/1).

Step B:

N-tert-Butoxycarbonyl-L-O-benzyltyrosinal

To a solution of N-tert-butoxycarbonyl-L-O-benzyltyrosine, N,O-dimethylhydroxamate (18.2 g, 44 mmol) in a 4:1 mixture of anhydrous diethylether and dimethoxyethane (300 ml) was added at 0° C., portionwise, lithium aluminum hydride (1.82 g, 48 mmol). Stirring was continued for 1.5 hours at 0° C. Hydrolysis was done by dropwise addition of a 1M solution of potassium hydrogeno sulphate (55 ml). The aqueous phase was decanted and reextracted with ethyl acetate (2×200 ml). The combined organic layers were washed with 3N hydrochloric acid (250 ml), water (200 ml), saturated sodium bicarbonate (150 ml) and brine (200 ml). The organic phase was dried over anhydrous magnesium sulphate. Filtration and removal of the solvent in vacuo yielded the expected aldehyde as a white solid. Recrystallization from ethyl acetate/pentane afforded 13 g of crystalline N-tert-butoxycarbonyl-L-O-benzyltyrosinal. Rf: 0.51 (silica gel, ethyl acetate/cyclohexane: 1/1).

Step C:

4-tert-Butoxycarbonylamino-2,2-difluoro-3-hydroxy-5 -(4-benzyloxy)phenylpentanoic acid, ethyl ester To a suspension of zinc (1.95 g, 30 matg) in anhydrous tetrahydrofuran (5 ml) was added, under nitrogen, a mixture of ethyl bromodifluoroacetate (6.09 g, 30 mmol) and N-tert-butoxycarbonyl-L-O-benzyltyrosinal (3.55 g, 10 mmol) in anhydrous tetrahydrofuran (25 ml). After addition of 2 ml of that solution, the suspension was heated at reflux with stirring. Gentle reflux was maintained by slow addition (dropwise) of the rest of the solution of aldehyde and bromoester. The mixture was stirred for 4 additional hours at room temperature after completion of the addition. Hydrolysis was performed by addition of 1M sulfuric acid (20 ml) and the mixture was extracted with ethyl acetate (3×50 ml). The combined organic layers were washed with brine and dried over anhydrous magnesium sulphate. Filtration and removal of the solvent in vacuo afforded an oil that was purified by flash chromatography (silica gel, gradient of ethyl acetate/cyclohexane: 1/9 to 3/7). 1.8 g of the title compound were isolated (38% yield). Rf: 0.55 and 0.5 (ethyl acetate/cyclohexane: 1/1). Analysis calculated for $C_{25}H_{31}NO_6F_2$: C, 62.62; H, 6.52; N, 2.92. Found: C, 62.81; H, 6.67; N, 3.05.

Step D:

4-tert-Butoxycarbonylamino-2,2-difluoro-3-hydroxy-5-(4-benzyloxy)phenyl-N-benzyl pentanamide To a solution of 4-tert-butoxycarbonylamino-2,2-difluoro-3-hydroxy-5-(4-benzyloxy)phenylpentanoic acid, ethyl ester (5.5 g, 11.5 mmol) in anhydrous tetrahydrofuran (50 ml) was added at 0° C., benzylamine (6.15 g, 57.5 mmol). The mixture was stirred for 3 hours at 0° C., then 15 hours at room temperature. The crude mixture was diluted with ethyl acetate (100 ml), washed twice with 0.1N aqueous hydrochloric acid (2×50 ml), water (50 ml), brine (50 ml). The organic layer was dried over anhydrous magnesium sulphate. Filtration and removal of the solvent in vacuo afforded a solid. Recrystallization from ethyl acetate/pentane yielded 5.17 g of the title compound as a white solid (83% yield). Rf: 0.45 (silica gel, ethyl acetate/cyclohexane: 1/1). Analysis calculated for $C_{30}H_{34}N_2O_5F_2$: C, 66.65; H, 6.34; N, 5.18. Found: C, 66.48; H, 6.45; N, 5.22.

Step E:

4-Amino-2,2-difluoro-3-hydroxy-5-(4-benzyloxy) phenyl-N-benzyl pentanamide

A solution of 4-tert-butoxycarbonylamino-2,2-difluoro-3 -hydroxy-5-(4-benzyloxy)phenyl-N-benzyl pentanamide (5.1 g, 9.4 mmol) in trifluoroacetic acid (100 ml) was stirred at 0° C. for 1 hour. The solvent was removed in vacuo. The residue was dissolved in ethyl acetate (100 ml). This solution was washed with saturated sodium bicarbonate (3×50 ml) and brine. The organic phase was dried over anhydrous magnesium sulphate. Filtration and removal of the solvent in vacuo yielded the title compound as a white solid which was used without further purification in the next step. When crystallized from ethyl acetate/pentane, an analytically pure sample could be obtained. Rf: 0.62 (silica gel, butanol/acetic acid/water: 6/2/2). Analysis calculated for $C_{25}H_{26}N_2O_3F_2$: C, 68.17; H, 5.95; N, 6.36. Found: C, 67.88; H, 5.88; N, 6.56.

Step F:

4-N-Benzyloxycarbonyl-L-valyl)amino-2,2-difluoro-3-hydroxy-5-(4-benzyloxy)phenyl-N-benzyl pentanamide To a solution of N-benzyloxycarbonyl-L-valine (0.251 g, 1 mmol) in anhydrous dichloromethane (15 ml) was added at 0° C., dicyclohexylcarbodiimide (0.206 g, 1 mmol) and N-hydroxybenzotriazole, hydrate (0.163 g, 1 mmol). To this mixture was added a solution of 4-amino-2,2-difluoro-3 -hydroxy-5-(4-benzyloxy)phenyl-N-benzyl pentanamide (0.44 g, 1 mmol) in anhydrous dimethylformamide (3 ml) at 0° C. Stirring was continued for 15 hours while temperature was allowed to raise to room temperature. Filtration of the precipitate and evaporation of the filtrate to dryness afforded a crude solid. Purification by flash chromatography (silica gel, ethyl acetate/cyclohexane: 2/8) afforded the title compound as a white solid (0.48 g, 71% yield). Rf: 0.41 and 0.29 (ethyl acetate/cyclohexane: 1/1).

Step G

4-N-Benzyloxycarbonyl-L-valyl)amino-2,2-difluoro-3-oxo-5-(4-benzyloxy)phenyl-N-benzylpentanamide To a solution of oxalyl chloride (0.173 g, 1.36 mmol) in anhydrous dichloromethane (1 ml) at −55° C., was added under nitrogen, dimethylsulfoxide (0.159 g, 2 mmol). After 10 minutes of stirring, was added to that mixture a solution of 4-(N-benzyloxycarbonyl-L-valyl)amino-2,2 -difluoro-3-hydroxy-5-(4-benzyloxy)phenyl-N-benzylpentanamide (0.23 g, 0.34 mmol) in dichloromethane (2 ml) and dimethylsulfoxide (1 ml). The mixture was stirred at −55° C., under nitrogen for 3 hours. The temperature was then allowed to raise to −20° C. Triethylamine (0.34 g, 3.4 mmol) was then added. The mixture was then stirred for 15 hours while the temperature was allowed to raise to room temperature. The crude mixture was taken off in ethyl acetate (20 ml) and washed with 0.1N aqueous hydrochloric acid (3×5 ml). The organic phase was washed with brine and dried over anhydrous magnesium sulphate. Filtration and removal of the solvent in vacuo yielded a crude residue which was purified by flash chromatography (silica gel, ethyl acetate/cyclohexane: 2/8). 0.16 g of the title compound was isolated. Recrystallization from ethyl acetate/pentane afforded 0.12 g of the pure material (white solid, 53% yield). Rf: 0.36 (ethyl acetate/cyclohexane: 1/1). Analysis calculated for $C_{38}H_{39}N_3O_6F_2$: C, 67.95; H, 5.85; N, 6.25. Found: C, 67.98; H, 5.82; N, 6.29.

EXAMPLE 2

4-BENZYLOXYCARBONYLAMINO-2,2-DIFLUORO-3-OXO-5-(4-BENZYLOXY)-PHENYL-N-BENZYL PENTANAMIDE

Step A:

4-Amino-2,2-difluoro-3-hydroxy-5-(4-benzyloxy)phenyl-N-benzyl pentanamide

A solution of 4-tert-butoxycarbonylamino-2,2-difluoro-3 -hydroxy-5-(4-benzyloxy)phenyl-N-benzyl pentanamide (5.1 g, 9.4 mmol) in trifluoroacetic acid (100 ml) was kept for 1 hour at 0° C. After removal of trifluoroacetic acid in vacuo, the residue was dissolved in ethyl acetate and the solution washed three times with a saturated solution of sodium bicarbonate. The organic phase was dried over anhydrous magnesium sulphate. Filtration and removal of the solvent in vacuo gave the title compound as a white solid which was used without further purification in the next step (3.0 g, 73% yield).

Step B:

4-Benzyloxycarbonylamino-2,2-difluoro-3-hydroxy-5-(4-benzyloxy)phenyl-N-benzyl pentanamide To a solution of the amine described in Example 2, Step A (0.22 g, 0.5 mmol) in anhydrous methanol (5 ml) at 0° C., was added slowly a solution of dibenzyl dicarbonate (0.143 g, 0.5 mmol) in anhydrous methanol (5 ml). The temperature was allowed to raise to room temperature and the mixture was kept at this temperature overnight. After removal of the solvent in vacuo, the solid residue was taken in a mixture of ether and pentane. Filtration and washing with pentane gave the title compound as a white solid (0.22 g, 77% yield). Rf: 0.43 (silica gel, ethyl acetate/cyclohexane: 1/1). Analysis calculated for $C_{33}H_{32}N_2O_5F_2-0.75 H_2O$ : C, 67.39; H, 5.74; N, 4.76. Found: C, 67.30; H, 5.51; N, 4.74.

Step C:

4-Benzyloxycarbonylamino-2,2-difluoro-3-oxo-5-(4-benzyloxy)-phenyl-N-benzyl pentanamide A mixture of the alcohol described in Example 2, Step B (0.09 g, 0.15 mmol), periodinane (0.085 g, 0.2 mmol) and tert-butanol (0.015 g, 0.2 mmol) in dry dichloromethane (5 ml) was stirred overnight at room temperature under nitrogen. After removal of the solvent in vacuo, the residue obtained was purified by flash chromatography (silica gel, 3.5 ethyl acetate/cyclohexane: 2/8). 0.077 g of the title compound were obtained (86% yield). Further purification by crystallization from ethyl acetate/pentane afforded the expected difluorostatone derivative as a white solid (0.048 g). Rf: 0.46 (ethyl acetate/cyclohexane: 1/1). Analysis calculated for $C_{33}H_{30}N_2O_5F_2-0.5 H_2O$: C, 68.15; H, 5.37; N, 4.82. Found: C, 68.42; H, 5.45; N, 4.93.

EXAMPLE 3

4-tert-BUTOXYCARBONYLAMINO-2,2-DIFLUORO-3-OXO-5-(4-BENZYLOXY)-PHENYL-N-BENZYL PENTANAMIDE The title compound was prepared from the alcohol of Example 1, Step D, by the procedure described in Example 2, Step C. (52% yield). Rf: 0.50 (silica gel, ethyl acetate/ cyclohexane: 1/1) Analysis calculated for $C_{30}H_{32}N_2O_5F_2$: C, 66.90; H, 5.99; N, 5.20. Found: C, 66.79; H, 5.88; N, 5.21.

EXAMPLE 4

4-N-BENZYLOXYCARBONYL-L-VALYL)AMINO-2,2-DIFLUORO-3-OXO-5-(4-BENZYLOXY)PHENYL-N-(TRIMETHYLSILYLMETHYL)PENTANAMIDE

Step A:

4-tert-Butoxycarbonylamino-2,2-difluoro-3-hydroxy-5-(4-benzyloxy)phenyl-N-trimethylsilylmethyl) pentanamide A solution of 0.24 g (0.5 mmol) of the ester described in Example 1, Step C in trimethylsilyl methylamine (0.8 ml) was heated overnight at 80° C. The excess amine was removed in vacuo and the residue (0.29 g) purified by flash chromatography (silica gel, ethyl acetate/petroleum ether: 3/7).

The title compound was obtained as a mixture of diastereoisomers (0.247 g, 92% yield). Rf: 0.34, 0.27 (ethyl acetate/petroleum ether: 3/7).

Step B:

4-amino-2,2-difluoro-3-hydroxy-5-(4-benzyloxy) phenyl-N-(trimethylsilylmethyl)pentanamide The title compound was prepared in 83% yield from the compound of Example 4, Step A, using the deprotection procedure described in Example 2, Step A.

Step C:

4-(N-Benzyloxycarbonyl-L-valyl)amino-2,2-difluoro-3-hydroxy-5-(4-benzyloxy)phenyl-N-(trimethylsilylmethyl)pentanamide To a stirred solution of N-benzyloxycarbonyl-L-valine anhydride [prepared from N-benzyloxycarbonyl-L-valine (0.219 g, 0.87 mmol) and dicyclohexylcarbodiimide (0.09 g, 0.436 mmol) for 45 minutes at room temperature and under nitrogen] in dry dimethylformamide (3.5 ml), were successively added 0.167 g (0.383 mmol) of the amine of Example 4, Step B, dissolved in dimethylformamide (4.5 ml), and 0.048 ml (0.436 mmol) of N-methylmorpholine. The reaction mixture was kept overnight at room temperature, diluted with water and extracted with ethyl acetate. The organic layer was then washed twice with a saturated solution of bicarbonate, twice with water, and dried over anhydrous sodium sulphate. Filtration, removal of the solvent in vacuo and purification of the residue by flash chromatography (silica gel, ethyl acetate/petroleum ether: 4/6) yielded the title compound as a white solid (0.12 g, mixture of diastereoisomers, 47% yield). Rf: 0.42, 0.26 (ethyl acetate/petroleum ether: 4/6).

Step D:

4-(N-Benzyloxycarbonyl-L-valyl)amino-2,2-difluoro-3-oxo-5-(4-benzyloxy)phenyl-N-(trimethylsilylmethyl)pentanamide The title compound was prepared from the alcohol of Example 4, Step C, following the oxidation procedure described in Example 1, Step G, but with two equivalents of dimethylsulfoxide relative to oxalyl chloride (59% yield). Rf: 0.49 (silica gel, ethyl acetate/petroleum ether: 4/6).

Analysis calculated for $C_{35}H_{43}N_3O_6SiF_2$–0.25 $H_2O$: C, 62.53; H, 6.52; N, 6.25. Found: C, 62.46; H, 6.47; N, 6.18.

EXAMPLE 5

4-(N-BENZYLOXYCARBONYL-L-VALYL)AMINO-2,2-DIFLUORO-3-OXO-5-(4-BENZYLOXY)PHENYL-N-PHENETHYL PENTANAMIDE

Step A:

4-tert-Butoxycarbonylamino-2,2-difluoro-3-hydroxy-5-(4-benzyloxy)phenyl-N-phenethyl pentanamide The ester of Example 1, Step C (0.4 g, 0.83 mmol) and phenethylamine (0.377 ml, 3 mmol) were heated under tetrahydrofuran reflux (2 ml) overnight. The solvent was evaporated and the obtained residue was dissolved in ethyl acetate. After washing with 1N hydrochloric acid (10 ml) and then washing with water until neutral, the organic layer was dried over anhydrous sodium sulphate, filtered off and concentrated in vacuo. The resulting solid (0.4 g) was purified by flash chromatography (silica gel, ethyl acetate/petroleum ether: 3/7). The title compound was obtained as a white solid (0.294 g, 53% yield), Rf: 0.23 (ethyl acetate/petroleum ether: 3/7).

Step B:

4-Amino-2,2-difluoro-3-oxo-5(4-benzyloxy)phenyl-N-phenethyl pentanamide

The title compound was obtained in 95% yield from the derivative of Example 5, Step A, using the procedure described in Example 2, Step A.

Step C:

4-N-Benzyloxycarbonyl-L-valyl)amino-2,2-difluoro-3-hydroxy-5-(4-benzyloxy)phenyl-N-phenethyl pentanamide The title compound was prepared from the amine of Example 5, Step B and N-benzyloxycarbonyl-L-valine as described in Example 4, Step C (71% yield). Rf: 0.28 (silica gel, ethyl acetate/dichloromethane: 1/9).

Step D:

4-(N-Benzyloxycarbonyl-L-valyl)amino-2,2-difluoro-3-oxo-5-(4-benzyloxy) phenyl-N-phenethyl pentanamide To a solution of the alcohol described in Example 5, Step C (0.242 g, 0.352 mmol) and dry dimethyl sulfoxide (0.4 ml; excess, for solubility reasons) in anhydrous dichloromethane (5 ml) at −30° C. was added dropwise under nitrogen a solution of oxalyl chloride (0.093 ml, 1.07 mmol) in anhydrous dichloromethane (1.5 ml). The mixture was stirred for 45 minutes at −30° C., cooled down to −70° C. just before the slow addition of ethyl diisopropylamine (0.556 ml, 3.2 mmol) and warmed up to 0° C. over a period of 15 minutes. The reaction mixture was diluted with dichloromethane and washed with 0.1N hydrochloric acid and then distilled water until neutral. After usual work-up, the residue (0.202 g) was purified by crystallization from dichloromethane/pentane to give the title compound as a white solid (0.086 g, 36% yield). Rf: 0.73 (silica gel, ethyl acetate/dichloromethane: 2/8). Analysis calculated for $C_{39}H_{41}N_3O_6F_2$–0.25 $H_2O$: C, 67.86; H, 6.06; N, 6.09. Found: C, 67.85; H, 6.08; N, 6.03.

EXAMPLE 6

4-N-BENZYLOXYCARBONYL-L-VALYL)AMINO-2,2-DIFLUORO-1,3-DIOXO-5-(4-BENZYLOXY)PHENYL-1-N-(1,2,3,4-TETRAHYDROISOQUINOLYL)-PENTANE

Step A:

4-tert-Butoxycarbonylamino-1-oxo-2,2-difluoro-3-hydroxy-5 -(4-benzyloxy)phenyl-1-(1,2,3,4-tetrahydroisoquinolyl)pentane The title compound was prepared from the ester of Example 1, Step C and 1,2,3,4-tetrahydroisoquinoline using the procedure described in Example 5, Step A (50% yield). Rf: 0.15 (silica gel, ethyl acetate/petroleum ether: 2/8).

Step B:

4-Amino-1-oxo-2,2-difluoro-3-hydroxy-5-(4-benzyloxy)phenyl-1-N-(1,2,3,4-tetrahydroisoquinol)pentane The title amine was prepared in 95% yield from the compound of Example 6, Step A, following the deprotection procedure described in Example 2, Step A.

Step C:

4-N-Benzyloxycarbonyl-L-valyl)amino-1-oxo-2,2-difluoro-3-hydroxy-5-(4-benzyloxy)phenyl-1-N-(1,2,3,4-tetrahydroisoquinolyl)pentane The title compound was prepared from the amine of Example 6, Step B and N-benzyloxycarbonyl-L-valine, following the coupling procedure described in Example 4, Step C (50% yield). Rf: 0.36 (silica gel, ethyl acetate/petroleum ether: 4/6).

Step D:

4-(N-Benzyloxycarbonyl-L-valyl)amino-2,2-difluoro-1,3-dioxo-5-(4-benzyloxy)phenyl-1-N-(1,2,3,4-tetrahydroisoquinolyl)-pentane The title compound was prepared in 62% yield from the hydroxy derivative of Example 6, Step C, using the oxidation procedure described in Example 5, Step D, but with two equivalents of dimethylsulfoxide relative to oxalyl chloride. Rf: 0.43 (silica gel, ethyl acetate/petroleum ether: 3/7). Analysis calculated for $C_{40}H_{41}N_3O_6F_2$–0.25 $H_2O$: C, 68.41; H, 5.96; N, 5.98. Found: C, 68.43; H, 5.92; N, 5.90.

EXAMPLE 7

4-(N-BENZYLOXYCARBONYL-L-VALYL) AMINO-2,2-DIFLUORO-3-OXO-5-(4-BENZYLOXY) PHENYL-N-(2-PYRIDYL)ETHYL PENTANAMIDE

Step A:

4-tert-Butoxycarbonylamino-2,2-difluoro-3-hydroxy-5-(4-benzyloxy)phenyl-N-(2-pyridyl)ethyl pentanamide The title compound was prepared from the ester of Example 1, Step C and 2-(2-aminoethyl)pyridine using the procedure described in Example 5, Step A (80% yield). Rf: 0.65, 0.56 (mixture of diastereoisomers, silica gel, ethyl acetate).

Step B:

4-Amino-2,2-diflouro-3-hydroxy-5-(4-benzyloxy)phenyl-N-(2 -pyridyl)ethyl pentanamide The title amine was prepared from the compound of Example 7, Step A, using the procedure described in Example 2, Step A (quantitative yield).

Step C:

4-(N-Benzyloxycarbonyl-L-valyl)amino-2,2-difluoro-3-hydroxy-5-(4-benzyloxy)phenyl-N-(2-pyridyl)ethyl pentamine The title compound was prepared from the amine of Example 7, Step B and N-benzyloxycarbonyl-L-valine following the coupling procedure described in Example 4, Step C (73% yield). Rf: 0.44 (silica gel, ethyl acetate/dichloromethane: 7/3).

Step D:

4-(N-benzyloxycarbonyl-L-valyl)amino-2,2-difluoro-3-oxo-5 -(4-benzyloxy)phenyl-N-(2-pyridyl)ethyl pentanamide The title compound was obtained in 62% yield from the hydroxy derivative of Example 7, Step C, using the oxidation procedure described in Example 5, Step D. Rf: 0.44 (silica gel, ethyl acetate/dichloromethane: 7/3. Analysis calculated for $C_{38}H_{40}N_4O_6F_2$–$H_2O$: C, 64.76; H, 6.01; N, 7.95. Found: C, 64.91; H, 5.73; N, 7.94.

EXAMPLE 8

4-N-QUINOLINE-2-CARBOXYL-L-VALYL) AMINO-2,2-DIFLUORO-3-OXO-5-(4-BENZYLOXY) PHENYL-N-(2-PYRIDYL)ETHYL PENTANAMIDE

Step A:

4-(N-tert-Butoxycarbonyl-L-valyl)amino-2,2-difluoro-3-hydroxy-5-(4-benzyloxy)phenyl-N-(2-pyridyl)ethyl pentanamide The title compound was prepared from the amine of Example 7, Step B and N-tert-butoxycarbonyl-L-valine using the symmetric anhydride coupling method similar to the one described with benzyloxycarbonyl-L-valine in Example 4, Step C (34% yield). Rf: 0.36 (silica gel, ethyl acetate/dichloromethane: 7/3).

Step B:

4-(L-valyl)amino-2,2-difluoro-3-hydroxy-5-(4-benzyloxy)phenyl-N-(2 -pyridyl)ethyl pentanamide A solution of 4-(N-tert-butoxycarbonyl-L-valyl)amino-2,2 -difluoro-3-hydroxy-5-(4-benzyloxy)phenyl-N-(2-pyridyl)ethyl pentanamide (0.1 g, 0.158 mmol) in formic acid (20 ml) was kept for 1.5 hours at room temperature. After removal of the formic acid in vacuo, the sticky residue was taken up in ethyl acetate, the organic solution washed with a saturated solution of sodium bicarbonate, and then distilled water until neutral. After usual work-up, the title compound was obtained as a white solid and used as such in the next step (0.085 g, quantitative yield).

Step C:

4-(N-Quinoline-2-carboxyl-L-valyl)amino-2,2-
difluoro-3-hydroxy-5-(4-benzyloxy)phenyl-N-
(2-pyridyl)ethyl pentanamide A solution of 2-quinoline carboxylic acid (0.027 g, 0.158 mmol) and N-methylmorpholine (0.017 ml, 0.158 mmol) in dry dimethylformamide (1 mmol) was cooled to −10° C. under nitrogen. After addition of neat ethylchloroformate (0.015 ml, 0.158 mmol) via syringe, the mixture was maintained at −10° C. for 1 hour. A solution of the amine of Example 8, Step B (0.085 g, 0.153 mmol) in anhydrous tetrahydrofuran (2 ml) was then added and the temperature was allowed to rise to 5° C. overnight. The reaction mixture was diluted with ethyl acetate and extracted twice with water. After usual work-up, the solid yellowish residue was purified by flash chromatography (silica gel, ethyl acetate). 0.098 g of the expected title compound was isolated as a white solid (87% yield). Rf: 0.34 (ethyl acetate).

Step D:

4-(N-Quinoline-2-carboxyl-L-valyl)amino-2,2-
difluoro-3-oxo-
5-(4-benzyloxy)phenyl-N-(2-pyridyl)ethyl
pentanamide The title compound was obtained from the alcohol derivative of Example 8, Step C using the Dess-Martin oxidation method described in Example 2, Step C (low yield, 20% due to incomplete conversion). Rf: 0.22 (silica gel, ethyl acetate/dichloromethane: 8/2).

EXAMPLE 9

N-[4-(N-BENZYLOXYCARBONYL-L-VALYL)
AMINO-2,2-DIFLUORO-1,3-DIOXO-5-
(4-BENZYLOXY)PHENYL-PENTYL]-L-
VALINALDEHYDE

Step A:

N-[4-N-tert-Butoxycarbonylamino-1-oxo-2,2-
difluoro-3-hydroxy-5-(4-benzyloxy)phenyl-pentyl]-
L-valinol The title compound was prepared from the ester of Example 1, Step C and L-valinol using the procedure described in Example 5, Step A (60% yield). Rf: 0.35 (silica gel, ethyl acetate/petroleum ether: 4/6).

Step B:

N-[4-Amino-1-oxo-2,2-difluoro-3-hydroxy-5-
(4-benzyloxy)phenyl-pentyl]-L-valinol The title amine was prepared as the trifluoroacetic acid salt from the derivative described in Example 9, Step A, using the method described in Example 2, Step A but without the basic extraction (85% yield).

Step C:

N-[4-(N-Benzyloxycarbonyl-L-valyl)amino-1-oxo-2,2-
difluoro-3-hydroxy-5-(4-benzyloxy)phenyl-pentyl]-
L-valinol The title compound was prepared from the salt of Example 9, Step B and N-benzyloxycarbonyl-L-valine using the symmetric anhydride coupling method described in Example 4, Step C (2 equivalents of N-methylmorpholine instead of 1; 74% yield).

Step D:

N-[4-(N-Benzyloxylcarbonyl-L-valyl)amino-2,2-
difluoro-1,3-dioxo-5-(4N-[-benzyloxy)phenyl-
pentyl]valinaldehyde The title difluorostatone derivative was prepared from the compound of Example 9, Step C using the procedure described in Example 5, Step D with the difference that equivalents of oxalyl chloride (and subsequent equivalents of the other reagents) were used instead of 3. The title compound has not been purified by chromatography but by crystallization from dichloromethane/pentane (61% yield). Analysis calculated for $C_{36}H_{41}N_3O_7F_2$–0.5 $H_2O$: C, 64.08; H, 6.27; n, 6.23. Found: C, 63.92; H, 6.25; N, 6.27.

EXAMPLE 10

4-(N-BENZYLOXYCARBONYL-L-tert-LEUCYL)
AMINO-2,2-DIFLUORO-3
-OXO-5-(4-BENZYLOXY)PHENYL-N-BENZYL
PENTANAMIDE Step A:

4-(N-Benzyloxycarbonyl-L-tert-leucyl)amino-2,2-
difluoro-3-hydroxy-5-(4-benzyloxy)phenyl-N-benzyl
pentanamide The title alcohol was prepared from the compound of Example 1, Step E and N-benzyloxycarbonyl-L-tert-leucine using the coupling method described in Example 4, Step C (81% yield). Rf: 0.50 (silica gel, ethyl acetate/petroleum ether: 4/6).

Step B:

4-(N-Benzyloxycarbonyl-L-tert-leucyl)amino-2,2-
difluoro-3-oxo-5-(4-benzyloxy)phenyl-N-benzyl
pentanamide The title compound was prepared from the alcohol of Example 10, Step A, following the oxidation procedure given in Example 5, Step D, but with two equivalents of dimethylsulfoxide relative to oxalyl chloride (83% yield). Rf: 0.50 (silica gel, ethyl acetate/petroleum ether: 4/6). Analysis calculated for $C_{39}H_{41}N_3O_6F_2$: C, 68.31; H, 6.03; N, 6.13. Found: C, 68.37; H, 6.10; N, 6.11.

EXAMPLE 11

4-[N-(4-NITROBENZYLOXYCARBONYL)-
L-VALYL]AMINO-2,2
-DIFLUORO-3-OXO-5-(4-BENZYLOXY)
PHENYL-N-BENZYL PENTANAMIDE

Step A:

4-[N-(4-Nitrobenzyloxycarbonyl)-L-valyl]amino-2,2-
difluoro-3-hydroxy-5-(4-benzyloxy)phenyl-N-benzyl
pentanamide The title alcohol was prepared from the compound of Example 1, Step E and N-(4-nitrobenzyloxycarbonyl)-L-valine following the coupling method described in Example 4, Step C (49% yield). Rf: 0.35 (silica gel, ethyl acetate/dichloromethane: 2/8).

Step B:

4-[N-(4-Nitrobenzyloxycarbonyl)-L-valyl]amino-2,2-difluoro-3-oxo-5-(4-benzyloxy)phenyl-N-benzyl pentanamide The title derivative was prepared from the compound of Example 11, Step A, using the Dess-Martin oxidation method given in Example 2, Step C (but with a larger excess of periodinane). It was purified by flash chromatography (silica gel, ethyl acetate/dichloromethane: 2/8, Rf: 0.35) and crystallization from acetone/pentane (46% yield). Analysis calculated for $C_{38}H_{38}N_4O_8N_2$: C, 63.38; H, 5.54; N, 7.82. Found: C, 63.49; H, 5.33; N, 7.75.

EXAMPLE 12

4-[N-(3-PYRIDYL)PROPIONYL-L-VALYL]AMINO-2,2-DIFLUORO-3-OXO-5-(4-BENZYLOXY)PHENYL-N-BENXYL PENTANAMIDE

Step A:

4-(N-tert-Butoxycarbonyl-L-valyl)amino-2,2-difluoro-3-hydroxy-5-(4-benzyloxy)phenyl-N-benzyl pentanamide The title compound was prepared in 81% yield from the amine of Example 1, Step E and N-tert-butoxycarbonyl-L-valine using the procedure described in Example 8, Step A. Rf: 0.40 (silica gel, ethyl acetate/cyclohexane: 1/1). Analysis calculated for $C_{35}H_{43}N_3O_6F_2$: C, 65.71; H, 6.77; N, 6.57. Found: C, 65.92; H, 6.87; N, 6.45.

Step B:

4-(L-Valyl)amino-2,2-difluoro-3-hydroxy-5-(4-benzyloxy)phenyl-N-benzyl pentanamide The title amine was prepared as the trifluoroacetic acid salt from the compound of Example 12, Step A using the method described in Example 2, Step A but without the basic extraction (quantitative yield).

Step C:

3-Pyridylpropionic acid

A solution of 3-(3-pyridyl)acrylic acid (3.8 g, 25 mmol) in 75 ml of distilled water was stirred at room temperature, in the presence of 10% palladium on charcoal (0.04 g), under a hydrogen atmosphere for 18 hours. The hydrogen atmosphere was changed to a nitrogen atmosphere and the catalyst filtered off. After removal of the solvent in vacuo, the residue was crystallized from hot ethanol to give the title acid in 87% yield (3.1 g).

Step D:

4-[N-(3-Pyridyl)propionyl-L-valyl]amino-2,2-difluoro-3-hydroxy-5-(4-benzyloxy)phenyl-N-benzyl pentanamide To a solution of 3-pyridylpropionic acid (0.196 g, 1.3 mmol) and N-methylmorpholine (0.177 g, 1.4 mmol) in anhydrous acetonitrile (20 ml) and anhydrous dimethylformamide (2 ml) at −20° C., under nitrogen, was added 0.0177 g of isobutylchloroformate (1.3 mmol). After 10 minutes at −20° C., a solution of the compound of Example 12, Step B (0.86 g, 1.3 mmol) in 3 ml of dry dimethylformamide and then N-methyl morpholine (0.141 g, 1.3 mmol) were added to the reaction mixture, which was kept at the same temperature for 2 more hours. The temperature was allowed to rise to room temperature while the stirring was continued overnight. The solvents were removed in vacuo and the residue was purified by flash chromatography (silica gel, ethyl acetate/methanol: 95/5) to afford the title compound as a solid which was crystallized from ethyl acetate/methanol/pentane (0.063 g, 57% yield). Rf: 0.36 (chloroform/methanol: 92/8). Analysis calculated for $C_{38}H_{42}N_4O_5F_2$–0.5 $H_2O$: C, 66.95; H, 6.36; N, 8.22. Found: C, 66.71; H, 6.19; N, 8.02.

Step E:

4-[N-(3-Pyridyl)propionyl-L-valyl]amino-2,2-difluoro-3-oxo-5-(4-benzyloxy)phenyl-N-benzyl pentanamide The title compound was prepared from the hydroxy derivative of Example 12 Step D following the oxidation procedure described in Example 1, Step G (41% yield). Rf: 0.41 (chloroform/methanol: 92/8). Analysis calculated for $C_{38}H_{40}N_4O_5F_2$–$H_2O$: C, 66.27; H, 6.15; N, 8.13. Found: C, 66.61; H, 6.07; N, 8.27.

EXAMPLE 13

4(N-BENZYLOXYCARBONYL-D,L-CYCLOPENTYLGLYCYL)AMINO-2,2-DIFLUORO-3-OXO-5-(4-BENZYLOXY)PHENYL-N-BENXYL PENTANAMIDE

Step A:

α-Cyclopentyl-tert-butylethylmalonate

A solution of tert-butylethylmalonate (5.65 g, 30 mmol) in anhydrous tetrahydrofuran (20 ml) was added to a suspension of sodium hydride—previously washed with pentane—(1.7 g, 32 mmol) in anhydrous tetrahydrofuran (30 ml). After heating at 60+ C. under nitrogen for 2 hours, a solution of cyclopentylbromide (4.47 g, 30 mmol) in dry tetrahydrofuran (20 ml) was added and the resulting mixture was kept for 40 hour s at the same temperature. Water hydrolysis, evaporation of the tetrahydrofuran in vacuo, extraction with distilled water and diethyl ether, and usual work-up gave the title compound which was purified by distillation (b.p.: 140° C./0.15 mmHg, 5.0 g, 72% yield).

Step B:

α-Cyclopentyl-monoethylmalonate

A solution of the diester of Example 13, Step A (3.8 g, 14.8 mmol) in 60 ml of trifluoroacetic acid was stirred for 1 hour at 0° C. After concentration in vacuo, the oily residue corresponding to the title compound was used as such in the next step (2.9 g).

Step C:

N-Benzyloxycarbonyl-D,L-cyclopentylglycine, ethyl ester

A solution of diphenylphosphoryl azide (4.4 g, 16 mmol) in anhydrous toluene (50 ml) was added dropwise at room temperature to a solution of the acid of Example 13, Step B (2.9 g, 14.5 mmol) and triethylamine (1.61 g, 16 mmol) in anhydrous toluene (50 ml). After stirring overnight at room temperature, benzyl alcohol was added (1.88 g, 17.4 mmol) and the mixture was heated under reflux for 20 hours. Washing of the organic solution with a 5% citric acid solution (3 times), distilled water, a saturated solution of sodium bicarbonate and finally brine, followed by usual work-up gave a residue which was purified by flash chromatography (silica gel, ethyl acetate/cyclohexane: 2/8) to afford the title compound as a yellow oil (2.5 g, 57% yield). Rf: 0.42 (ethyl acetate/cyclohexane: 1/1).

Step D:

N-Benzyloxycarbonyl-D,L-cyclopentylglycine

A mixture of the ester of Example 13, Step C (2.46 g, 8 mmol) and lithium hydroxyde (0.67 g, 16 mmol) in dimethoxyethane (30 ml) and distilled water (20 ml) was stirred overnight at room temperature. The reaction mixture was diluted with distilled water and extracted with ethyl acetate. The aqueous layer was acidified until pH 2 with 3N hydrochloric acid, saturated with sodium chloride, and extracted three times with ethyl acetate. Usual work-up of the organic layers and crystallization of the residue from diethyl ether/pentane gave the title derivative as a white solid (1.75 g, 77% yield).

Step E:

4-(N-Benzyloxycarbonyl-D,L-cyclopentylglycyl) amino-2,2-difluoro- 3-hydroxy-5-(4-benzyloxy)phenyl-N-benzyl pentanamide The title compound was obtained from the acid of Example 13, Step D and the amine of Example 1, Step E, following the coupling procedure described in Example 12, Step D, by using only one equivalent of N-methylmorpholine instead of two (53% yield). Rf: 0.42 (silica gel, ethyl acetate/cyclohexane: 1/1). Analysis calculated for $C_{40}H_{43}N_3O_6F_2$: C, 68.65; H, 6.19; N, 6.00. Found: C, 68.13; H, 5.95; N, 5.95.

Step F:

4-(N-Benzyloxycarbonyl-D,L-cyclopentylycyl) amino-2,2 -difluoro-3-oxo-5-(4-benzyloxy)phenyl-N-benzyl pentanamide The title difluorostatone derivative was obtained in 50% yield from the alcohol of Example 13, Step E using the oxidation procedure described in Example 1, Step G, but with two equivalents of dimethylsulfoxide relative to oxalyl chloride. Analysis calculated for $C_{40}H_{41}N_3O_6F_2$–0.5 $H_2O$: C, 67.98; H, 5.99; N, 5.95 Found: C, 67.91; H, 5.87; N, 5.97.

EXAMPLE 14

4-N-BENZYLOXYCARBONYL-D,L-CYCLOHEXYLGLYCYL)AMINO-2,2-DIFLUORO-3-OXO-5-(4-BENZYLOXY) PHENYL-N-BENXYL PENTANAMIDE

Step A:

α-Cyclohexyl-tert-butylethylmalonate

The title compound was prepared from tert-butylethylmalonate and cyclohexyl iodide using the procedure described in Example 13, Step A (b.p.: 120° C./0.07 mmHg, 61% yield).

Step B:

α-Cyclohexyl-monoethylmalonate

The title compound was prepared from the diester of Example 14, Step A, using the procedure described in Example 13, Step B (94% yield).

Step C:

N-Benzyloxycarbonyl-D,L-cyclohexylglycine, ethyl ester

Step C:
The title derivative was prepared from the ester of Example 14, Step B, following the procedure described in Example 13, Step C (72% yield). Rf: 0.46 (silica gel, ethyl acetate/cyclohexane: 1/1).

Step D:

N-Benzyloxycarbonyl-D,L-cyclohexylglycine

The title compound was prepared from the ester of Example 14, Step C, using the procedure described in Example 13, Step D (89% yield).

Step E:

4-(N-Benzyloxycarbonyl-D,L-cyclohexylglycyl) amino-2,2 -difluoro-3-hydroxy-5-(4-benzyloxy)phenyl-N-benzyl pentanamide The title compound was prepared from the acid of Example 14, Step D and the amine of Example 1, Step E, following the coupling procedure described in Example 12, Step B, by using only one equivalent of N-methylmorpholine, instead of two (67% yield). Rf: 0.40 (silica gel, ethyl acetate/cyclohexane: 1/1). Analysis calculated for $C_{41}H_{45}N_3O_6F_2$: C, 67.71; H, 6.49; N, 5.78. Found: C, 67.74; H, 6.25; N, 5.72.

Step F:

4-(N-Benzyloxycarbonyl-D,L-cyclohexylglycyl) amino-2,2 -difluoro-3-oxo-5-(4-benzyloxy)phenyl-N-benzyl pentanamide The title derivative was prepared in 45% yield from the alcohol of Example 14, Step E, using the Swern oxidation described in Example 1, Step G, but with two equivalents of dimethylsulfoxide relative to oxalyl chloride. Rf: 0.43 (silica gel, ethyl acetate/cyclohexane: 1/1) m.p.: 178°–179° C. Analysis calculated for $C_{41}H_{43}N_3O_6F_2$: C, 69.18; H, 6.09; N, 5.90. Found: C, 69.23; H, 6.10, N, 5.98.

EXAMPLE 15

N-[4-(N-BENZYLOXYCARBONYL-L-VALYL) AMINO-2,2-DIFLUORO-1,3 -DIOXO-5-(4-BENZYLOXY) PHENYL-PENTYL]MORPHOLINE

Step A:

N-[4-N-tert-butoxycarbonylamino-1-oxo-2,2-difluoro-3-hydroxy-5 -(4-benzyloxy)phenyl-pentyl]morpholine The title compound was prepared from the ester of Example 1, Step C and morpholine (10 equivalents) using the procedure described in Example 5, Step A (77% yield). Rf: 0.27, 0.22, mixture of diastereoisomers (silica gel., ethyl acetate/cyclohexane: 1/1).

23

Step B:

N-[4-Amino-1-oxo-2,2-difluoro-3-hydroxy-5-
(4-benzyloxy)phenyl-pentyl]morpholine The title amine was obtained in 88% yield from the compound of Example 15, Step A, using the procedure described in Example 2, Step A.

Step C:

N-[4-(N-Benzyloxycarbonyl-L-valyl)amino-1-oxo-2,2-
difluoro-3-hydroxy-5-(4-benzyloxy)phenyl-pentyl]
morpholine The title compound was prepared from the amine of Example 15, Step B and N-benzyloxycarbonyl-L-valine using the symmetric anhydride coupling method described in Example 4, Step C (51% yield). MH$^+$: 654, MNH$_4^+$: 671.

Step D:

N-[4-(N-Benzyloxycarbonyl-L-valyl)amino-2,2-
difluoro-1,3
-dioxo-5-(4-benzyloxy)phenyl-pentyl]morpholine The title difluorostatone derivative was obtained in 56% yield from the alcohol of Example 15, Step C, using the oxidation procedure described in Example 1, Step G, but with two equivalents of dimethylsulfoxide relative to oxalyl chloride. Rf: 0.33 (silica gel, ethyl acetate/cyclohexane: 1/1). Analysis calculated for $C_{35}H_{39}N_3O_7F_2$: C, 64.50; H, 6.03; N, 6.45. Found: C, 64.28; H, 6.03; N, 6.60.

EXAMPLE 16

4-(N-BENZYLOXYCARBONYL-L-VALYL)AMINO-
2,2-DIFLUORO-3-OXO-5-(4-BENZYLOXY)
PHENYL-N-BENZYL-N-METHYL
PENTANAMIDE

Step A:

4-tert-Butoxycarbonylamino-2,2-difluoro-3-hydroxy-5-(4
-benzyloxy)phenyl-N-benzyl-N-methyl
pentanamide First method:
The title compound was prepared from the ester of Example 1, Step C and N-methylbenzylamine, using the method described in Example 1, Step D (51% yield). Rf: 0.54, 0.50; mixture of diastereoisomers (silica gel, ethyl acetate/cyclohexane: 1/1).

Second method:
The title compound was obtained from the ester of Example 1, Step C in two steps. The ester was transformed into the corresponding acid (using the procedure described in Example 13, Step D) which was then coupled with N-methylbenzylamine following the procedure described in Example 12, Step D (overall yield: 67%).

Step B:

4-Amino-2,2-difluoro-3-hydroxy-5-(4-benzyloxy)
phenyl-N-benzyl-N-methyl pentanamide The title amine was prepared in 88% yield from the compound of Example 16, Step A using the method described in Example 2, Step A.

Step C:

4-N-Benzyloxycarbonyl-L-valyl)amino-2,2
-difluoro-3
-hydroxy-5-(4-benzyloxy)phenyl-N-benzyl-N-methyl
pentanamide The title compound was obtained in 30% yield from the amine of Example 16, Step B and N-benzyloxycarbonyl-L-valine, using the coupling method described in Example 4, Step C. Rf: 0.37 (silica gel, ethyl acetate/cyclohexane: 1/1). m.p.:152° C. Analysis calculated for $C_{39}H_{43}N_3O_6F_2$: C, 68.11; H, 6.30; N, 6.11. Found: C, 67.74; H, 6.24; N, 6.12.

Step D:

4-(N-Benzyloxycarbonyl-L-valyl)amino-2,2-difluoro-
3-oxo-5-(4-benzyloxy)phenyl-N-benzyl-N-methyl
pentanamide The title compound was obtained from the hydroxyl derivative of Example 16, Step C, using the procedure described in Example 1, Step G, but with two equivalents of dimethylsulfoxide relative to oxalyl chloride (43% yield). Rf: 0.50 (silica gel, ethyl acetate/cyclohexane: 1/1). Analysis calculated for $C_{39}H_{41}N_3O_6F_2$: C, 68.31; H, 6.03; N, 6.13. Found: C, 68.17; H, 5.99; N, 6.01.

EXAMPLE 17

4-(N-BENZYLOXYCARBONYL-L-VALYL)
AMINO-2,2-DIFLUORO-3-OXO-5
-(4-BENZYLOXY)PHENYL-N-(3-PYRIDYL)
METHYL PENTANAMIDE

Step A:

4-tert-Butoxycarbonylamino-2,2-difluoro-3-hydroxy-
5-(4-benzyloxy)phenyl-N-(3-pyridyl)methyl
pentanamide The title compound was prepared from the ester of Example 1, Step C and 3-(aminomethyl)pyridine using the procedure described in Example 5, Step A (76% yield). Rf: 0.4 (silica gel, ethyl acetate).

Step B:

4-Amino-2,2-difluoro-3-hydroxy-5-(4-benzyloxy)
phenyl-N-(3-pyridyl)methyl pentanamide The title amine was prepared from the compound of Example 17, Step A, using the method of Example 8, Step B, with sodium carbonate instead of sodium bicarbonate as the base (quantitative yield).

Step C:

4-(N-Benzyloxycarbonyl-L-valyl)amino-2,2-difluoro-3
-hydroxy-5-(4-benzyloxy)phenyl-N-(3-pyridyl)methyl
pentanamide To a solution of N-benzyloxycarbonyl-L-valine anhydride (0.145 g, 0.3 mmol) in anhydrous dichloromethane (3 ml) was added a solution of the amine of Example 17, Step B (0.132 g, 0.3 mmol) in 2 ml of dry dichloromethane and 0.033 ml of N-methylmorpholine (0.3 mmol). The reaction mixture was stirred at room temperature under nitrogen overnight and then concentrated in vacuo. The residue was dissolved in a large amount of ethyl acetate and extracted with distilled water. Usual work-up and purification of the resulting solid by flash chromatography (silica gel, ethyl acetate/dichloromethane: 7/3 with 2% of methanol) gave the title compound as a white solid (0.085 g, 42% yield). Rf:

0.28 (ethyl acetate/dichloromethane: 7/3 with 2% of methanol).

Step D:

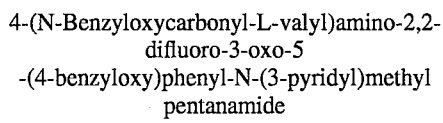

4-(N-Benzyloxycarbonyl-L-valyl)amino-2,2-difluoro-3-oxo-5
-(4-benzyloxy)phenyl-N-(3-pyridyl)methyl
pentanamide The title compound was obtained in 42% yield from the alcohol of Example 17, Step C, using the oxidation procedure described in Example 5, Step D. Rf: 0.4 (silica gel, ethyl acetate/petroleum ether: 9/1). Analysis calculated for $C_{37}H_{38}F_2N_4O_6$–0.5 $H_2O$: C, 65.19; H, 5.77; N, 8.22. Found: C, 65.43; H, 5.88; N, 8.33.

EXAMPLE 18

N-[4-(N-BENZYLOXYCARBONYL-L-VALYL)
AMINO-2,2-DIFLUORO-1,3
-DIOXO-5-(4-BENZYLOXY)PHENYL-PENTYL]-
(O-BENZYL)-L-VALINOL

Step A:

N-tert-Butoxycarbonyl-L-valinol

A solution of valinol (1.03 g, 10 mmol) and di-tert-butyl dicarbonate (2.4 g, 11 mmol) in methanol (10 ml) was kept for 1 hour at room temperature. After concentration in vacuo, the residue was purified by flash chromatography (silica gel, ethyl acetate/petroleum ether: 1/1) to give the title compound in quantitative yield. Rf: 0.36 (ethyl acetate/petroleum ether: 1/1).

Step B:

N-tert-Butoxycarbonyl-O-benzyl-L-valinol

To a solution of the alcohol of Example 18, Step A (2.03 g, 10 mmol) and benzylbromide (1.33 ml, 11.2 mmol) in anhydrous tetrahydrofuran (25 ml) was added at 0° C. and under nitrogen, potassium-tert-butoxide (1.5 g, 13.4 mmol) as a solid, in small portions. The reaction mixture was stirred for 2 hours at room temperature, diluted with ether, extracted with a 1N solution of potassium hydrogenosulphate and washed twice with distilled water. After usual work-up, the resulting oil was purified by flash chromatography (silica gel, ethyl acetate/petroleum ether: 1/9) to give the title compound (1.34 g, 46% yield). Rf: 0.73 (ethyl acetate/petroleum ether: 1/1).

Step C:

O-Benzyl-L-valinol

The title compound was prepared from the derivative of Example 18, Step B, using the deprotection procedure described in Example 8, Step B (92% yield).

Step D:

N-[4-tert-Butoxycarbonylamino-1-oxo-2,2-difluoro-3-hydroxy-
5-(4-benzyloxy)phenyl-pentyl]-(O-benzyl)-L-valinol The title compound was prepared from the ester of Example 1, Step C and O-benzyl-L-valinol using the procedure described in Example 5, Step A (56% yield). Rf: 0.49 (silica gel, ethyl acetate/petroleum ether: 3/7).

Step E:

N-[4-Amino-1-oxo-2,2-diflouro-3-hydroxy-5-
(4-benzyloxy)phenyl-pentyl]-(O-benzyl)-L-valinol The title amine was prepared in 87% yield from the compound of Example 18, Step D, using the procedure described in Example 8, Step B.

Step F:

N-[4-(N-Benzyloxycarbonyl-L-valyl)-amino-1-oxo-2,2
-difluoro-3-hydroxy-5-(4-benzyloxy)phenyl-pentyl]-
(O-benzyl)-L-valinol The title compound was prepared from the amine of Example 18, Step E and N-benzyloxycarbonyl-L-valine anhydride, following the coupling procedure described Example 17, Step C (82% yield). Rf: 0.21 (silica gel, ethyl acetate/petroleum ether: 3/7).

Step G:

N-[4-(N-Benzyloxycarbonyl-L-valyl)amino-2,2-
difluoro-1,3-dioxo-5-(4-benzyloxy)phenyl-pentyl]-
(O-benzyl)-L-valinol The title difluorostatone derivative was obtained from the alcohol of Example 18, Step F, using the Swern oxidation method given in Example 5, Step D, but with 5 equivalents of oxalyl chloride (and subsequent equivalents of the other reagents) instead of 3 and with two equivalents of dimethylsulfoxide relative to oxalyl chloride ( 56% yield). Rf: 0.54 (silica gel, ethyl acetate/dichloromethane: 2/8). Analysis calculated for $C_{43}H_{49}F_2N_3O_7$: C, 68.15; H, 6.52; N, 5.54. Found: C, 67.96; H, 6.64; N, 5.44.

EXAMPLE 19

4-(N-BENZYLOXYCARBONYL-L-tert-LEUCYL)
AMINO-2,2-DIFLUORO-3
-OXO-5-(4-BENZYLOXY)PHENYL-N-(3-PYRIDYL)
METHYL PENTANAMIDE Step A:

4-(N-Benzyloxycarbonyl-L-tert-leucyl)amino-2,2-
difluoro-3-hydroxyl-
5-(4-benzyloxy)phenyl-N-(3-pyridyl)methyl
pentanamide The title compound was prepared from the amine of Example 17, Step B and N-benzyloxycarbonyl-tert-L-leucine anhydride, using the procedure described in Example 17, Step C (86% yield). Rf: 0.46 (silica gel, ethyl acetate/dichloromethane: 7/3 with 3% methanol).

Step B:

4-(N-Benzyloxycarbonyl-L-tert-leucyl)amino-2,2-
difluoro-3
-oxo-5-(4-benzyloxy)phenyl-N-(3-pyridyl)methyl
pentanamide The title compound was prepared in 86% yield from the alcohol of Example 19, Step A, using the oxidation method described in Example 1, Step G, but with 10 equivalents of oxalyl chloride (and subsequent equivalents of the other reagents) instead of 4 and with two equivalents of dimethylsulfoxide relative to oxalyl chloride. Rf: 0.38 (silica gel, ethyl acetate/dichloromethane: 9/1). Analysis calculated for $C_{38}H_4N_4O_6F_2$: C, 66.46; H, 5.87; N, 8.16. Found: C, 66.43; H, 5.91; N, 8.09.

EXAMPLE 20

4-(N-BENZYLOXYCARBONYL-L-VALYL) AMINO-2,2-DIFLUORO-3-OXO-5-(4-BENZYLOXY) PHENYL-N-PIPERONYLPENTANAMIDE

Step A:

4-tert-Butoxycarbonylamino-2,2-difluoro-3-hydroxy-5-(4-benzyloxy)phenyl-N-piperonyl pentanamide The title compound was obtained from the ester described in Example 1, Step C and piperonylamine using the procedure described in Example 5, Step A (74% yield). Rf: 0.31 (silica gel, ethyl acetate/petroleum ether: 3/7).

Step B:

4-Amino-2,2-difluoro-3-hydroxy-5-(4-benzyloxy)-phenyl-N-piperonyl pentanamide

The title amine was prepared in quantitative yield from the compound of Example 20, Step A, following the method described in Example 8, Step B.

Step C:

4-(N-Benzyloxycarbonyl-L-valyl)amino-2,2-difluoro-3-hydroxy-5-(4-benzyloxy)phenyl-N-piperonyl pentanamide The title compound was obtained from the amine of Example 20, Step B and N-benzyloxycarbonyl-L-valine anhydride using the procedure described in Example 17, Step C (78% yield). Rf: 0.64 (silica gel, ethyl acetate/dichloromethane: 3/7).

Step D:

4-(N-Benzyloxycarbonyl-L-valyl)amino-2,2-difluoro-3-oxo-5 -(4-benzyloxy)phenyl-N-piperonyl pentanamide The title difluorostatone derivative was prepared from the alcohol of Example 20, Step C, using the procedure described in Example 5, Step D but with 10 equivalents of dimethylsulfoxide and subsequent equivalents of the other reagents instead of 3 (58% yield). Rf: 0.38 (silica gel, ethyl acetate/dichloromethane: 2/8) Analysis calculated for $C_{39}H_{39}N_3O_5F_2$; C, 65.45; H, 5.49; N, 587. Found: C, 65.47; H, 5.54; N, 5.82.

EXAMPLE 21

N-[4-(N-BENZYLOXYCARBONYL-L-VALYL) AMINO-2,2-DIFLUORO-1,3 -DIOXO-5-(4-BENZYLOXY)PHENYL-PENTYL]-(O-BENZYL)-D-VALINOL

Step A:

N-tert-Butoxycarbonyl-D-valinol

The title compound was obtained in quantitative yield from D-valinol and di-tert-butyldicarbonate using the procedure described in Example 18, Step A.

Step B:

N-tert-Butoxycarbonyl-O-benzyl-D-valinol

The title derivative was prepared from the alcohol of Example 21, Step A and benzyl bromide, following the procedure described in Example 18, Step B (47% yield). Rf: 0.73 (silica gel, ethyl acetate/petroleum ether: 1/1).

Step C:

O-Benzyl-D-valinol

The title compound was prepared from the derivative of Example 21, Step B, using the deprotection method described in Example 8, Step B (71% yield).

Step D:

N-[4-tert-Butoxycarbonylamino-1-oxo-2,2-difluoro-3-hydroxy-5 -(4-benzyloxy)phenyl-pentyl]-(O-benzyl)-D-valinol The title compound was prepared from the ester of Example 1, Step C and O-benzyl-D-valinol using the procedure described in Example 5, Step A (54% yield). Rf: 0.49 (silica gel, ethyl acetate/petroleum ether: 3/7).

Step E:

N-[4-Amino-1-oxo-2,2-difluoro-3-hydroxy-5 (4-benzyloxy)phenyl-pentyl]-(O-benzyl)-D-valinol The title amine was prepared in 96% yield from the compound of Example 21, Step D, using the procedure described in Example 8, Step B.

Step F:

N-[4-(N-Benzyloxycarbonyl-L-valyl)amino-1-oxo-2,2-difluoro-3-hydroxy-5(4-benzyloxy)phenyl-phenyl]-(O-benzyl)-D-valinol The title compound was prepared from the amine of Example 21, Step E and N-benzyloxycarbonyl-L-valine anhydride, following the coupling procedure described in Example 17, Step C (70% yield). Rf: 0.48 (silica gel, ethyl acetate/petroleum ether: 4/6).

Step G:

N-[4-(N-Benzyloxycarbonyl-L-valyl)amino-2,2-difluoro-1,3 -dioxo-5-(4-benzyloxy)phenyl-pentyl]-(O-benzyl)-D-valinol The title compound was obtained from the alcohol of Example 21, Step F, using the Swern oxidation method described in Example 5, Step D, but with 5 equivalents of oxalyl chloride instead of 3 and with 2 equivalents of dimethyl sulfoxide relative to oxalyl chloride (61% yield). Rf: 0.48 (silica gel, ethyl acetate/petroleum ether: 2/8). Analysis calculated for $C_{43}H_{49}F_2N_3O_7$: C, 68.15; H, 6.52; N, 5.54. Found: C, 67.73; H, 6.44; N, 5.37.

The compounds of the present invention are useful as inhibitors of retroviral proteases required for replication, particularly the HIV-1 and HIV-2 viral proteases, the prevention or treatment of infection by the human immunodeficiency virus (HIV), and the treatment of consequent pathological conditions such as the acquired immunodeficiency syndrome (AIDS) in mammals capable of being infected with HIV virus. Treating AIDS, preventing infection by HIV or treating infection by HIV, is defined as including, but not limited to, treating a wide range of states of HIV infection: AIDS, ARC (AIDS related complex), both symptomatic and asymptomatic, and actual or potential exposure to HIV. For example, the compounds of this invention are useful in preventing infection by HIV after suspected past exposure to HIV by, e.g., blood transfusion, accidental needle stick, or exposure to patient blood during surgery.

In the present invention, compounds with asymmetric centers may occur as racemates, racemic mixtures and as individual diastereomers, with all isomeric forms of the compounds being included in the present invention.

For these purposes, the compounds of the present invention may be administered orally, parenterally (including subcutaneous injections, intravenous, intra-muscular, transdermal, intrasternal injection or infusion techniques), by inhalation spray, or rectally, in dosage unit formulations containing convention non-toxic pharmaceutically acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories) or they may be administered transdermally.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetener/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidize and/or dissolve in the rectal cavity to release the drug.

Dosage levels of the order of 0.02 to 5.0 or 10.0 grams per day are useful in the treatment or prevention of the above-indicated conditions, with oral doses two to five times higher. For example, infection by HIV is effectively treated by the administration of from 10 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of Excretion, drug combination the severity of the particular condition, and the host undergoing therapy.

The present invention is also directed to combinations of the HIV protease-inhibitory compounds with one or more agents useful in the treatment of AIDS, such as, for example, with known antiviral agents suitable for treating HIV 1 and HIV 2 viral infections, e.g., AZT, with or without a PNPase inhibitor, or in conjunctive therapy with DDI and a PNPase inhibitor.

The compounds of this invention may be assayed for their HIV-protease inhibition using the following published techniques.

Preparation of Retroviral Enzyme and

Assay for Inhibition of the Protease

A) Preparation of Retroviral Enzyme To prepare the recombinant protease, the HIV protease was expressed via *E. Coli* by the published work of C. Guénet, et al., in European Journal of Pharmacology, Molecular Pharmacology Section, 172 (1989) 443–451.

B) Assay for Inhibition of Recombinant Vital Protease inhibition of the reaction of the synthetic protease [amino acid residues 69–167 of the pol open reading frame in Ratner, L. et al., *Nature*, 313, 277 (1985) and synthesized by Merrifield solid-phase synthesis] with a peptide substrate [Ser-Gln-Asn-Tyr-Pro-Ile-Val-$NH_2$, 2 mg/ml when the reaction is initiated] were in 50 mM Na acetate, pH 5.5, at 30° C. for 1 hour. Various concentrations of inhibitor in 1.0 µl DMSO were added to 36 µl of assay solution and the reaction initiated by the addition of 4 µ(1.6 µg) of synthetic protease. The reaction was quenched with 160 µl of 12% acetic acid. Products of the reaction were separated by HPLC (VYDAC wide pore 5 cm C-18 reverse phase, acetonitrile gradient, 0.1% trifluoroacetic acid). The extent of inhibition of the reaction was determined from the peak heights of the products. HPLC of the products, independently synthesized, provided quantitation standards and confirmation of the product composition.

By following the techniques referenced above, as well as by utilization of other known techniques, as well as by comparison with compounds known to be useful for treatment of the above-mentioned disease states, it is believed that adequate material is available to enable one of ordinary skill in the art to practice the invention.

As is true for most classes of compounds found to be useful in the pharmaceutical industry, certain subgeneric groups and certain specific compounds are more preferred. Within the concepts of this invention, it is to be found that the preferred compounds are those wherein $R_1$ is benzyl oxy,

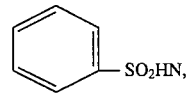

(3-pyridyl)ethyl, isoquinolyl, 4-alkoxybenzyloxy, or morpholyl, $P_2$ is isopropyl, cyclopentyl, 2-(4,4-difluoro)-pyrrolidyl, 2-hydroxy-2-propyl, t-butyl, $P_1$ is piperonyl, 4-(benzyloxy)benzyl, 3-(benzyloxy)benzyl, (4-benzyloxy-3-methoxy)benzyl, when $R_5$ is H, $R_6$ is benzyl, piperonyl, $CH_2$-pyridyl, 4-(benzyloxy)benzyl, morpholino, tetrahydroisoquinolyl, 4-(3-hydroxypropyl)benzyl, 2-(3-hydroxypropyl)benzyl, and

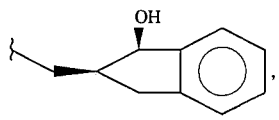

or —CH(Y)(Z) with Y and Z both being as generally defined, but particularly when Y is isopropyl, preferably in the D configuration, or phenyl and when Z is benzyloxymethylene, CHO, COOH, alkoxy or $COOR_4$, when $R_5$ is other than H it is preferred that $R_5$ be methyl, 4-hydroxybutyl or 3-hydroxypropyl and that $R_6$ be benzoxy or benzyl, and when $R_5$ and $R_6$ form a heterocyclic moiety with the nitrogen attached thereto, it is preferred that

and morpholino be the heterocyclic moieties. The preferred specific compounds are those shown in the chart below and those products which are exemplified above, particularly the product of Example 1.

| $R_1$ | $P_2$ | $P_1$ | $R_5$ = H, $R_6$ |
|---|---|---|---|
| benzyloxy | isopropyl | piperonyl | benzyl |
| benzyloxy | isopropyl | piperonyl | piperonyl |
| phenyl-$SO_2NH$ | isopropyl | 4-(benzyloxy)benzyl | benzyl |
| benzyloxy | isopropyl | 3-(benzyloxy)benzyl | benzyl |
| benzyloxy | t-butyl | 3-(benzyloxy)benzyl | benzyl |
| benzyloxy | isopropyl | (4-benzyloxy-3-methoxy)benzyl | benzyl |
| benzyloxy | isopropyl | (4-benzyloxy-3-methoxy)benzyl | piperonyl |
| benzyloxy | 2-hydroxy-2-propyl | 4-(benzyloxy)benzyl | benzyl |
| (3-pyridyl)ethyl | isopropyl | 4-(benzyloxy)benzyl | —$CH_2$-(3-pyridyl) |
| isoquinolyl | isopropyl | 4-(benzyloxy)benzyl | —$CH_2$-(3-pyridyl) |
| (3-pyridyl)ethyl | isopropyl | 4-(benzyloxy)benzyl | —$C_2H_5$-(2-pyridyl) |
| (3-pyridyl)ethyl | isopropyl | 4-(benzyloxy)benzyl | —$CH_2$-(2-pyridyl) |
| benzyloxy | t-butyl | 4-(benzyloxy)benzyl | isobutyl-$CH_2$-O-benzyl (D) |
| benzyloxy | isopropyl | 4-(benzyloxy)benzyl | CH(phenyl)CHO |
| (3-pyridyl)ethyl | isopropyl | 4-(benzyloxy)benzyl | CH(phenyl)CHO |
| isoquinolyl | isopropyl | 4-(benzyloxy)benzyl | isobutyl-$CH(OCH_3)$ (D) |
| benzyloxy | isopropyl | 4-(benzyloxy)benzyl | isobutyl-$CH(OCH_3)$ (D) |

| $R_1$ | $P_2$ | $P_1$ | $R_5$, $R_6$ |
|---|---|---|---|
| benzyloxy | isopropyl | 4-(benzyloxy)benzyl | phenyl-CH(CO$_2$H)- (L) |
| benzyloxy | isopropyl | 4-(benzyloxy)benzyl | 4-(benzyloxy)benzyl |
| benzyloxy | t-butyl | 4-(benzyloxy)benzyl | 4-(benzyloxy)benzyl |
| (3-pyridyl)ethyl | isopropyl | 4-(benzyloxy)benzyl | 4-(benzyloxy)benzyl |
| benzyloxy | isopropyl | 4-(benzyloxy)benzyl | phenyl-CH(CO$_2$-t-Bu)- (L) |
| benzyloxy | isopropyl | 4-(benzyloxy)benzyl | isopropyl-CH(CO$_2$H)- (L) |
| 4-O-methyl-benzyloxy | isopropyl | 4-(benzyloxy)benzyl | benzyl |
| benzyloxy | isopropyl | 4-(benzyloxy)benzyl | morpholyl (—N(CH$_2$CH$_2$)$_2$O) |
| benzyloxy | isopropyl | 4-(benzyloxy)benzyl | 4-(3-hydroxy-propyl)benzyl |
| benzyloxy | isopropyl | 4-(benzyloxy)benzyl | 2-(3-hydroxy-propyl)benzyl |
| benzyloxy | isopropyl | 4-(benzyloxy)benzyl | 1-hydroxy-indanyl |

| $R_1$ | $P_2$ | $P_1$ | $R_5$, $R_6$ |
|---|---|---|---|
| benzyloxy | isopropyl | 4-(benzyloxy)benzyl | $R_5$ = CH$_3$, $R_6$ = —O-phenyl |
| (3-pyridyl)ethyl | isopropyl | 4-(benzyloxy)benzyl | $R_5$ = CH$_3$, $R_6$ = benzyl |
| (3-pyridyl)ethyl | cyclopentyl | 4-(benzyloxy)benzyl | $R_5$ = CH$_3$, $R_6$ = benzyl |
| benzyloxy | 2-(4,4-difluoro)pyrrolidyl | 4-(benzyloxy)benzyl | $R_5$ = CH$_3$, $R_6$ = benzyl |
| morpholyl | isopropyl | 4-(benzyloxy)benzyl | $R_5$ = CH$_3$, $R_6$ = benzyl |
| (3-pyridyl)ethyl | isopropyl | 4-(benzyloxy)benzyl | $R_5$ = 4-hydroxybutyl, $R_6$ = benzyl |
| benzyloxy | isopropyl | 4-(benzyloxy)benzyl | $R_5$ = 3-hydroxypropyl, $R_6$ = benzyl |
| (3-pyridyl)ethyl | isopropyl | 4-(benzyloxy)benzyl | $R_5$, $R_6$ = morpholyl |
| (3-pyridyl)ethyl | cyclopentyl | 4-(benzyloxy)benzyl | $R_5$, $R_6$ = morpholyl |
| benzyloxy | isopropyl | 4-(benzyloxy)benzyl | $R_5$, $R_6$ = —N(CH$_2$CH$_2$)$_2$NCHO |
| (3-pyridyl)ethyl | isopropyl | 4-(benzyloxy)benzyl | tetrahydro-isoquinolyl |

What is claimed is:
1. A compound of the formula

$$R_1 \left[ \begin{array}{c} P_2 \\ | \\ CNHCH \\ \| \\ O \end{array} \right]_x \begin{array}{c} P_1 \\ | \\ CNHCHC-CF_2C-NR_5R_6 \\ \| \quad \| \quad \| \\ O \quad O \quad O \end{array} \qquad I$$

and the hydrates, isosteres and the pharmaceutically acceptable salts thereof wherein x is zero or one,
$P_1$ is Q, or B, B being

[structure: $CH_2$—phenyl—$[(CH_2)_a$—$(O)_b$—$(CH_2)_c$—$R]_d$]

with the proviso that B is other than p-hydroxybenzyl or p-alkoxybenzyl,
a is zero, or 1, 2 or 3,
b is zero or 1,
c is zero or 1, 2, 3, 4 or 5,
d is 1 or 2,
e is zero, 1 or 2,
Q is

[structure: $(CH_2)_d$—benzodioxole—$(CH_2)_d$]

$P_2$ is $C_{1-6}$ alkyl, cyclopentyl, cyclohexyl, hydroxy $C_{1-6}$ alkylene, or

[structure: cyclic with F, F and N—T]

with T being H or $C(O)R_4$,
R is —$CH_2CHO$, hydroxy $C_{1-6}$ alkylene, $C_{1-6}$ alkoxy $C_{1-6}$ alkylene, $C_{1-6}$ alkyl, phenyl

[structure: phenyl—$(R_3)_d$]

or Q,
$R_1$ is benzyloxy, $C_{1-6}$ alkoxy, $C_{1-6}$ alkyl, phenyl, benzyl, phenethyl, fluorenylmethylenoxy, 2-isoquinolinyl, PDL, $CH_2N$—$(CH_2)_3CH_2$,  $O$—$(CH_2)_2$—$N$—$CH_2CH_2$, $NHSO_2R_4$, $N(R_4)$(benzyl),
and $N(R_4)$(PDL), with PDL being —$(CH_2)_a$-2-, -3-, or 4-pyridyl, or p-W-substituted benzyloxy with W being nitro, OH amino, $C_{1-6}$ alkoxy, or hydroxy $C_{1-6}$ alkylene, or halogeno,
$R_3$ is $C_{1-6}$ allenyl $C_{1-6}$ alkoxy, $C_{1-6}$ alkoxy $C_{1-6}$ alkylene, hydroxy $C_{1-6}$ alkylene, $C_{1-6}$ alkyl, H, or OH, $R_4$ is H, $C_{1-6}$ alkyl, phenyl or benzyl
$R_5$ is H, $C_{1-6}$ alkyl, OH, $C_{1-6}$ alkoxy,

[structure: —$(CH_2)_d$—phenyl—$(V)_e$,]

V being $OR_4$ or hydroxy $C_{1-6}$ alkylene, $CH_2Si(CH_3)_2(R_3)$, —$(CH_2)_d$—Q, PDL, —N—$(CH_2)_2$—O—$CH_2CH_2$,  [indanol structure with HO and $(CH_2)_b$],

[structure: $CH_2$—benzimidazole],

—$(C_{1-6}$ alkylene-$)OR_4$ or —$CH(Y)(Z)$, Y being hydroxy $C_{1-6}$ alkylene, $C_{1-6}$ alkyl, or —$(CH_2)_e$—$C_6H_4$—$(V)_e$, and Z being CHO, $CO_2R_4$, $CO_2NHR_4$ or —$(CH_2)_e$—$OR_4$,
$R_6$ is as defined for $R_5$ with the proviso that $R_6$ is other than H when $R_5$ is H, and when $R_5$ and $R_6$ are taken together with nitrogen atom to which they are attached form a heterocyclic moiety of the formulae

—N$(CH_2)_3CH_2$,  —N$(CH_2)_4CH_2$,  —N$(CH_2)_2OCH_2CH_2$, (a)  (b)  (c)

[structure (d): N—$CH_2$—phenyl—$(CH_2)_b$],  [structure (e): $R_3$—Si with $R_3$, N—$R_7$], (d)  (e)

[structure (f): decalin with H, H, N—CH₃, $R_7$]  or  —N$(CH_2)_2N$—$CH_2CH_2$, | CH(O)

(f)  (g)

—$NCH_2C(CH_2)_2CH_2$,  or  —N—$(CH_2)_2CCH_2CH_2$,
      $\|$                         $\|$
      $R_8$                       $R_8$ (h)  (i)

$R_7$ is $CH_2OR_4$ or $C(O)NHR_4$,
$R_8$ (H,OH) or =O.

2. A compound of claim 1 wherein x is one.
3. A compound of claim 2 wherein $P_1$ is B.
4. A compound of claim 2 wherein $P_1$ is Q.
5. A compound of claim 1 wherein x is one, $R_1$ is benzyloxy,

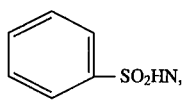

(3-pyridyl)ethyl, isoquinolyl, 4-alkoxybenzyloxy, or morpholyl, $P_2$ is isopropyl, cyclopentyl, 2-(4,4-difluoro)pyrrolidyl, 2-hydroxy-2-propyl, t-butyl, $P_1$ is piperonyl, 4-(benzyloxy)benzyl, 3-(benzyloxy)benzyl, (4-benzyloxy-3-methoxy)benzyl, when $R_5$ is H, $R_6$ is benzyl, piperonyl, —$CH_2$-pyridyl, 4-(benzyloxy)benzyl, morpholino, tetrahydroisoquinolyl, 4-(3-hydroxypropyl)benzyl, 2-(3-hydroxypropyl)benzyl,

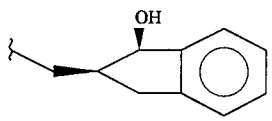

or CH(Y)(Z).

6. A compound of claim 5 wherein $R_1$ is benzyloxy, $P_2$ is isopropyl or 2-hydroxy-2-propyl, $P_1$ is piperonyl, $R_5$ is H and $R_6$ is benzyl or piperonyl.

7. A compound of claim 1 wherein $R_1$ is benzyloxy, $P_2$ is isopropyl, $P_1$ is 4-(benzyloxy)benzyl, $R_5$ is H and $R_6$ is benzyl.

8. A compound of claim 1 wherein $R_1$ is —$NHSO_2$phenyl, $P_2$ is isopropyl, $P_1$ is 4-(benzyloxy)benzyl, $R_5$ is H and $R_6$ is benzyl.

9. A compound of claim 1 wherein $R_1$ is benzyloxy, $P_2$ is t-butyl, $P_1$ is benzyloxybenzyl, $R_5$ is H and $R_6$ is benzyl.

10. A compound of claim 1 which is N-[4-(N-benzyloxycarbonyl-L-valyl)amino-2,2-difluoro-1,3-dioxo-5-(4-benzyloxy)phenyl-pentyl]-(O-benzyl)-D-valinol.

11. A pharmaceutical composition comprising a compound according to claim 1, optionally in combination with a pharmaceutically acceptable carrier.

* * * * *

UNITED STATES PATENT AND TRADEMARK OFFICE
CERTIFICATE OF CORRECTION

PATENT NO. : 5,559,140

DATED : September 24, 1996

INVENTOR(S) : Daniel Schirlin; Viviane Van Dorsselaer; Celine Tarnus

It is certified that error appears in the above-identified patent and that said Letters Patent is hereby corrected as shown below:

Column 7, Line 45 of Patent reads "Pmoieties" and should read --$P_2$ moieties --.

Column 7, Line 57 of Patent reads "and being P'$_2$" and should read -- P'$_2$ being --.

Column 12, Line 50 of Patent reads "gel, 3.5 ethyl" and should read -- gel, ethyl --.

Column 17, Line 9 of Patent reads "(1 mmol)" and should read -- (1 ml) --.

Column 18, Line 9 of Patent reads "that equivalents" and should read -- that 5 equivalents --.

Column 19, Line 19 of Patent reads "BENXYL" and should read --BENZYLOXY--.

Column 20, Line 26 of Patent reads "BENXYL" and should read --BENZYLOXY--.

Column 20, Line 36 of Patent reads "60+ C." and should read -- 60° C --.

Column 21, Line 35 of Patent reads "cyclopentylcyl" and should read -- cyclopentylglycyl --.

Column 21, Line 52 of Patent reads "BENXYL" and should read -- BENZYL --.

Column 26, Line 66 of Patent reads "$H_4$" and should read -- $H_{40}$ --.

Column 27, Line 45 of Patent reads "$O_5$" and should read -- $O_8$ --.

Column 28, Line 29 of Patent reads "phenyl-phenyl" and should read -- phenyl-pentyl --.

Signed and Sealed this

Twentieth Day of January, 1998

Attest:

BRUCE LEHMAN

*Attesting Officer*  *Commissioner of Patents and Trademarks*